(12) United States Patent
Bobek

(10) Patent No.: US 7,271,239 B2
(45) Date of Patent: Sep. 18, 2007

(54) D-ISOMERS OF ANTIMICROBIAL PEPTIDE

(75) Inventor: Libuse A. Bobek, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 124 days.

(21) Appl. No.: 11/213,245

(22) Filed: Aug. 26, 2005

(65) Prior Publication Data

US 2006/0069022 A1    Mar. 30, 2006

Related U.S. Application Data

(60) Provisional application No. 60/606,312, filed on Sep. 1, 2004.

(51) Int. Cl.
*A61K 31/10* (2006.01)
*A61K 38/00* (2006.01)
(52) U.S. Cl. ............................... 530/327; 514/14
(58) Field of Classification Search ............ 514/14
See application file for complete search history.

(56) References Cited

U.S. PATENT DOCUMENTS 6,790,833 B2    9/2004    Bobek

OTHER PUBLICATIONS

Gururaja, et al., Candidacidal Activity Prompted by N-Terminus Histatin-like Domain of Human Salivary Mucin (MUC-7), BBA 1431 (1999) pp. 107-119.
Satyanarayana, et al., Divergent Solid-phase Synthesis and Candidacidal Activity of MUC7 D1, a 51-Residue Histidine-rich N-terminal Domain of Human Salivary Mucin (MUC7), J. Peptide Res., 2000, 56, pp. 275-282.

*Primary Examiner*—Karen Cochrane Carlson
*Assistant Examiner*—Suzanne M. Noakes

(74) *Attorney, Agent, or Firm*—Hodgson Russ LLP

(57) ABSTRACT

This invention provides D-isomers of MUC7-12-mer peptide of human saliva MUC7. The isomers have antimicrobial activity comparable to that of the L-isomers and are resistant to proteolysis. These peptides can be used as antifungal and antimicrobial agents.

14 Claims, 13 Drawing Sheets

SEQUENCE LISTING

```
<160> NUMBER OF SEQ ID NOS: 4

<210> SEQ ID NO 1
<211> LENGTH: 12
<212> TYPE: PRT
<213> ORGANISM: Homo sapiens
<220> FEATURE:
<223> OTHER INFORMATION: 12-mer; Amino acids 40-51 of the MUC7D1
      peptide.

<400> SEQUENCE: 1

Arg Lys Ser Tyr Lys Cys Leu His Lys Arg Cys Arg
                5                   10

<210> SEQ ID NO 2
<211> LENGTH: 12
<212> TYPE: PRT
<213> ORGANISM: Homo sapiens
<220> FEATURE:
<223> OTHER INFORMATION: Histatin-5, 12-mer

<400> SEQUENCE: 2

Ala Lys Arg His His Gly Tyr Lys Arg Lys Phe His
                5                   10
```

```
<210> SEQ ID NO 3
<211> LENGTH: 23
<212> TYPE: PRT
<213> ORGANISM: Homo sapiens
<220> FEATURE:
<223> OTHER INFORMATION: Magainin II

<400> SEQUENCE: 3

Gly Ile Gly Lys Phe Leu His Ser Ala Lys Lys Phe Gly Lys Ala
                  5                  10                  15

Phe Val Gly Glu Ile Met Asn Ser
                20

<210> SEQ ID NO 4
<211> LENGTH: 20
<212> TYPE: PRT
<213> ORGANISM: Homo sapiens
<220> FEATURE:
<223> OTHER INFORMATION: 20-mer; Amino acids 32-51 of the MUC7D1
      peptide.

<400> SEQUENCE: 4

Leu Ala His Gln Lys Pro Phe Ile Arg Lys Ser Tyr Lys Cys Leu
                  5                  10                  15

His Lys Arg Cys Arg
                20
```

D-ISOMERS OF ANTIMICROBIAL PEPTIDE

This application claims priority to U.S. provisional application No. 60/606,312, filed on Sep. 1, 2004, the disclosure of which is incorporated herein by reference.

This work was supported by grant DE09820 from the National Institute of Dental and Craniofacial Research (NIH/NIDCR). The Government has certain rights in the invention.

FIELD OF THE INVENTION

The present invention relates generally to the field of antimicrobial agents.

BACKGROUND OF THE INVENTION

Invasive fungal infections are still the cause of major complications in immunocompromised patients (patients receiving immunosuppressive therapy—such as bone marrow and organ transplant recipients, cancer patients, and HIV/AIDS patients). Due to the emergence of pathogens resistant to conventional antifungals agents and toxicity of some antimycotics, intense efforts are being made in antifungal drug discovery to develop more promising and effective antifungal agents for clinical use.

Many currently available and clinically used antimicrobial drugs have undesirable toxic and other side effects. In addition, a wide-spread use of these drugs has lead to the rapid development of drug-resistant strains which are the main cause for the treatment failures. Thus, development and delivery of new antimicrobial agents with different mechanism of action, low toxicity and low tendency to elicit resistance is urgently needed. Among other approaches, naturally occurring cationic antimicrobial peptides is attracting increasing attention. This is because unlike many currently used antimicrobial compounds (CAMPs), they show little or no toxicity toward mammalian cells and low tendency to elicit resistance.

We have previously shown that peptides derived from the N-terminal region of the low molecular mass human salivary mucin, MUC7, have a significant and a broadspectrum fungicidal and bactericidal activity in vitro, as determined by killing assays in phosphate buffer (1-3). A further study showed that MUC7 12-mer (amino acids 40-51 of the parent MUC7, with net charge of +6) is the optimal size peptide fragment that possesses potent antifungal activity against *Candida albicans* and *Cryptococcus neoformans* (4). A clear correlation between the net positive charge of the MUC7 12-mer, its potency and initial interaction of peptide with fungal cells was found by killing assays, fluorescence microscopy and fungal cell-membrane potential measurements, although the killing mechanism is not fully understood. MUC7 12-mer possesses antifungal activity in LYM (modified, low salt RPMI 1640 medium) and also exhibits synergistic antifungal effects in vitro with Histatin5 12-mer (Hsn5 12-mer) or miconazole (5).

Information on the antimicrobial activity of the CAMPs in vivo is very limited. To initiate in vivo investigation of the potential of the MUC7 and other antimicrobial peptides as therapeutic agents for use against oral candidiasis, one needs to determine whether or not the peptides retain their activity in saliva. Saliva is a natural ecological environment of oral cavity and some components in saliva may affect therapeutic use of the peptides in vivo. In particular, it is suggested that peptides administered in vivo may be degraded by certain proteases present in saliva, leading to diminishing or loss of their antimicrobial activity. These proteases may come from the host or microorganism in the oral cavity. It has been demonstrated in vitro that the antimicrobial peptides can be degraded by proteases, resulting in decrease or loss of their antimicrobial biological activity (3, 6-8). It is well know that the degradation of proteins or peptides can be prevented by protease inhibitors. It has been suggested that degradation can be also decreased or prevented by modifying molecular structure of peptides by substitution of the natural L-amino acids with D-forms because natural proteases recognize only the natural L-amino acids. Therefore, studies have been conducted aimed at introducing D-amino acids into CAMPs. However, such studies indicate that introduction of D-amino acids into cationic antimicrobial peptides can have either a positive and negative effects on the activity. For example, introduction of three D-amino acids into Magainin-II produced a diastereomer (peptide containing both L- and D-amino acids) with no antimicrobial (antiprotozoan) activity (9). A lack of activity was also observed with other diastereomers (10). On the other hand, all D amino acid Magainin-II exhibited antibacterial potency nearly identical to that of the all-L-enantiomer and was highly resistant to proteolysis and non-hemolytic (11). Similarly, all D-amino acid 11 residue peptide derived from human granulysin (residues 32-42) was resistant to proteolysis and retained the bacteriocidal activity of the L-peptide (12). All D-amino acid isomer of Hsn5 12-mer (known as P113-D) was as active against *C. albicans* as the natural L-form. In addition, the peptide was active in the presence of sputum from cystic fibrosis patients against respiratory bacteria, while the activity of the L-form was basically lost (13). These studies emphasize the uncertain outcome of using D-isomers and also underline the need for development of new effective antimicrobial agents that are both active and resistant to proteolysis.

SUMMARY OF THE INVENTION

The present invention provides D-isomers of a 12-mer antimicrobial peptide (RKSYKCLHKRCR—SEQ ID NO:1). In one embodiment, all the amino acids in the peptide are D-amino acids. This peptide has candidacidal activity in physiological-like conditions (especially those found in the oral cavity) and is resistant to proteolysis. The D-isomers can be used as an antimicrobial agents. Data is presented in an animal model for oral candidiasis to demonstrate the effectiveness of this peptide against fungal infection. Data is also presented to demonstrate the usefulness of this peptide for selective inhibition of microbes which can form a biofilm in the oral cavity.

DETAILED DESCRIPTION OF THE INVENTION

Figure 1:
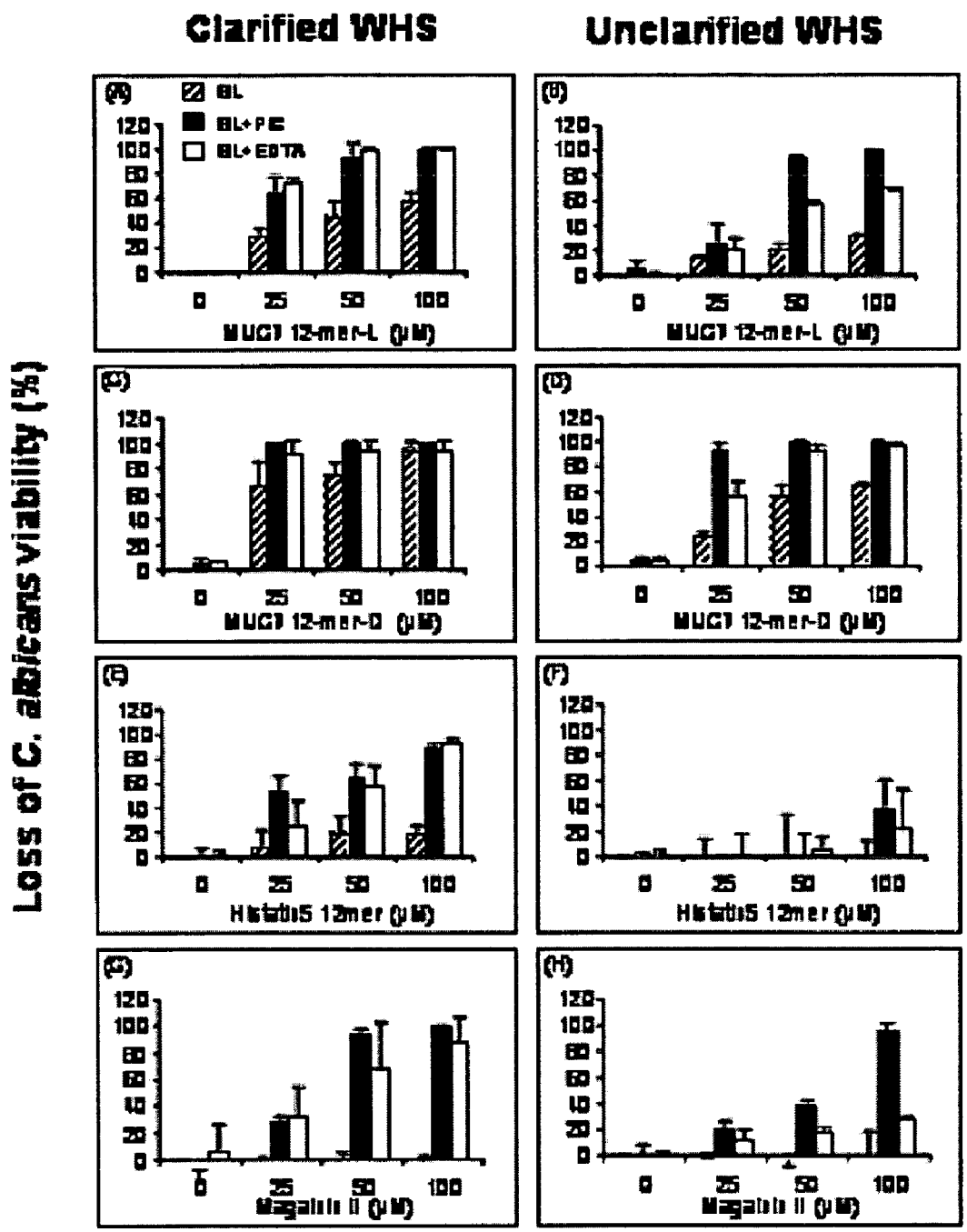
FIG. 1. Candidacidal activity of MUC7 12-mer-L, MUC7 12-mer-D, Hsn5 12-mer, and Magainin-II in whole human saliva (WHS). Each peptide at final concentration of 25, 50, and 100 µM was incubated with *C. albicans* (DIS isolate at $1\times10^5$ cells/ml) and 20 µl of clarified or unclarified saliva (SL; hatched bars), saliva containing Protease inhibitor cocktail (PIC) (SL+PIC; filled bars), or saliva containing ethylenediamine tetraacetic acid (EDTA) (SL+EDTA; clear bars) at 37° C. for 1.5 h. At the end of incubation, the samples were diluted 20-fold and aliquots plated on SDA. The colony forming units (CFU) were counted after 24 h of incubation. The loss of *C. albicans* viability was determined by the equation (1−CFU of the test group/CFU of the control group)×100%. The data represent three individual trials, and in each trial the sample was duplicated; the error bars represent standard deviation.

This invention provides antimicrobial peptides comprising the sequence RKSYKCLHKRCR (SEQ ID NO:1) in which one or more amino acids are D-isomers. Also provided are methods for use of these peptides as antimicrobial agents. The number of D-amino acids in the peptide should be such that the peptide is significantly resistant to proteolysis and has at least 90% activity of the L-amino acid peptide. In one embodiment, the peptide has all D-amino acids.

The peptides of the present invention can be formulated into compositions in pharmaceutically acceptable carriers for administration to individuals. For oral administration, the peptides can be formulated into a solid preparation such as tablets, pills, granules, powder, capsules and the like, or a liquid preparation such as a solution, suspension, emulsion and the like. The pharmaceutical preparations for oral administration comprising one or more peptides of the present invention may also contain one or more of the following customary excipients: fillers and extenders including starches, lactose, sucrose, glucose, mannitol and silica; binders including carboxymethylcellulose, alginates, gelatine and polyvinylpyrrolidone; humectants including glycerine; disintegrating agents, including agar—agar, calcium carbonate and sodium carbonate; solution retarders, including paraffin; absorption accelerators including quaternary ammonium compound; wetting agents including cetyl alcohol or glycerine monostearate; adsorbents including kaolin and bentonite; lubricants including talc, calcium stearate and magnesium stearate and solid polyethylene glycols; colorants; flavourings; and sweeteners.

In one embodiment, the peptides of the present invention can be used with a protease inhibitor cocktail which comprises EDTA. In another embodiment, the peptides can be used with EDTA without the protease inhibitors.

When the preparation is used for parental administration, the preparation is made in an injection formula. For the preparation of an injection formula, the solutions and emulsions can be in a sterile form which is isotonic with blood. The suspensions can contain in addition to the active peptide or peptides, preservatives, stabilizers, solubilizers, wetting agents, salts for changing the osmotic pressure or buffers.

The peptides of the present invention are useful as antifungal or antibacterial agents. The 12-mer peptides can be used against a broad spectrum of fungi and bacteria including, but not limited to, *Candida albicans, Candida glabrata* and their azole resistant counterparts, *Cryptococus neoformans* and its amphotericin B-resistant counterpart, *Candida krusei, Saccharomyces cerevisiae*, and against *E. coli, Streptoccocus gordonii, Streptococcus mutans, Actinobacillus actinomycetemcimitans* and *P. gingivalis*. The optimal concentrations of the peptides can be obtained by determining the minimum inhibition concentrations (MICs) against bacteria and fungi. At the same time, toxicity studies can be carried out in vitro using cell culture techniques, in animals and by simple techniques such as the ability of the peptides to lyse blood. The advantages of the present invention will become clear from the following examples which are meant to be illustrative and are not intended to be restrictive in any way.

The peptides of the present invention have been found to be particularly useful in inhibiting the biofilm formed by *S. mutans* in the oral cavity. Thus, these peptides can be used for initiating the degradation of, or preventing the formation of bacterial biofilms in the oral cavity. In one embodiment, the peptide formulation of the present invention is delivered locally to the oral cavity.

This invention will be further understood by the Examples presented below which are intended to be illustrative and not restrictive.

EXAMPLE 1

Materials and Methods

Fungal strains and growth media. *C. albicans* DIS was kindly provided by M. Edgerton, Department of Biology, State University of New York, Buffalo. *C. albicans* ATCC 96112, *C. glabrata* ATCC 90030, were purchased from ATCC. An azole-resistant clinical isolate of *C. glabrata* 65C was kindly provided by John E. Bennett, National Institute of Allergy and Infectious Diseases, Bethesda, Md.). A clinical isolate of *C. krusei* was obtained from the Erie County Medical Center, Buffalo, N.Y. The fungal strains were stored at $-80°$ C. in glycerol. For each experiment, cells were cultured freshly from frozen stock on Sabouraud Dextrose Agar (SDA, Difco) for 24 hours at $37°$ C. To prepare fungal cell, one colony was picked from the plate and resuspended in 10 mM sodium phosphate buffer (pH 7.4). The concentration was adjusted to $1\times10^5$ cells/ml for the antifungal activity assay.

Peptides. MUC7 12-mer-L (RKSYKCLHKRCR (SEQ ID NO:1), residues 40-51 of the parent MUC7), MUC7 12-mer-D (all 12 L-form amino acids replaced by D-form), Hsn5 12-mer (AKRHHGYKRKFH—SEQ ID NO:2, residues 4-15 of the parent Hsn5, also known as P113 (19)), and Magainin II (24 residue peptide of following sequence GIGKFLHSAKKFGKAFVGEIMNS—SEQ ID NO:3) were custom-synthesized by Bio-Synthesis (Lewisville, Tex.). HPLC and mass spectrometry assays were performed by company to analyze the purity of the peptides. The purity (70-100%) was taken into consideration in preparation of the stock solution of each peptide for antifungal assays. The peptides were dissolved in sterile dd-water at 1 mg/mL; aliquots were freeze-dried and stored at $-20°$ C. For each experiment, the freeze-dried peptides were re-dissolved at 5 or 10 mg/mL in sterile double distilled (dd)-water.

Protease inhibitors. Protease Inhibitor Cocktail (P-2714) was purchased from Sigma Chemical Co. (St. Louis, Mo.). It was prepared as 10× by dissolving the powder in 10 ml of sterile dd-water, and stored in $-20°$ C. 1×PIC contains 2 mM 4-(2-aminoethyl)benzenesulfonyl fluoride (AEBSF), 1 mM EDTA, 130 µM Bestatin, 14 µM E-64, 1 µM Leupeptin, and 0.3 µM Aprotinin (Ap). EDTA was purchased from J.T. Baker Chemical Co. (Philipsburg, N.J.); 0.2M solution was prepared by dissolving EDTA powder in sterile dd-water.

Killing assays in saliva. Unclarified saliva (unstimulated whole saliva) was collected from five healthy individuals during the fasting. Clarified saliva was obtained by passing the unclarified saliva through the 0.2 µm pore size sterile syringe filter (VWR scientific products, West Chester, Pa.). Candidacidal activity assays were performed as described previously (4), except the phosphate buffer was substituted with saliva. Briefly, to determine the optimal concentration of peptide on candidacidal activity in saliva, 20 µl of two-fold serial dilutions of peptides in saliva (to give final peptide concentrations of 25, 50, and 100 µM), or saliva containing 1×PIC, or saliva containing 1 mM EDTA, were incubated in duplicate with an equal volume (20 µl) of fungal cell suspension (105 cell/ml) in 10 mM phosphate buffer (PB), pH 7.2. Saliva without peptides was a blank control. After incubation at $37°$ C. for 1.5 h, the reactions were diluted 20-fold in PB and aliquots (50 µl, ~120 cells) of each sample were plated on SDA. The plates were incubated at $37°$ C. for 1 day aerobically and the number of colony-forming units (CFUs) was counted. Percentage of killing was calculated as (1−amount of viable cells in the test group)/(amount of viable cells in the control group)×100%.

Time kill experiments. Time-kill curves in saliva were determined by incubation of *C. albicans* with MUC7 12-mer-L or D (50 µM final concentration). At different time points (0, 5, 15, 30, 45, and 90 min), cells were diluted 20-fold in 10 mM sodium phosphate buffer and plated on SDA plates to determine the number of CFUs.

Stability of peptides in saliva and susceptibility of septides to trypsin. Three microliters of each peptide (MUC7 12-mer-D, MUC7 12-mer-L, Hsn5 12-mer, or Magainin-II, at 1 µg/µl in 0.2 M Tris-HCl buffer pH 7.5) were incubated with 11 µl of 0.2 µg/ml trypsin or saliva. This gave a final concentration of 0.16 µg/ml for trypsin, and 0.2 µg/µl for peptides (or 127, 127, 128, and 81 µM, for MUC7 12-mer-D, MUC7 12-mer-L, Hsn5 12-mer, or Magainin II, respectively). The reactions, without PIC (water instead or PIC) or with 1×PIC [50% (v/v)] were incubated 0.5 h with trypsin, and 1 hr with saliva (clarified or unclarified) at 37° C. The control of each compound was also incubated with Tris-HCl buffer in parallel. The samples were analyzed by 13% SDS-PAGE. Gels was stained with Coomassie brilliant blue R-250 and further analyzed for the peptide degradation by GS-700 Imaging Densitometer (Bio Red). The degradation was estimated by the equation: 1−(density of test band/density of control band)×100%.

Hemolytic assay. Hemolysis of MUC7 12-mer-D and PIC was examined as described previously (5). Amphotericin B and 12-mer-L were used as controls.

Statistics. Each value was determined from two independent experiments performed in duplicate. Wilcoxon signed-ranks test was performed by using SPSS software to compare the mean difference between PIC and non-PIC groups. The peptides are considered to have statistically significant difference in candidacidal activity if P<0.05. 9

Cell culture. The HOK-16B cell line (originated from primary normal human keratinocytes) was kindly provided by No-Hee Park, UCLA School of Dentistry. The KB cell line was obtained from the American Type Culture Collection (CLL-17). Cells were maintained in keratinocyte growth medium (KGM; Clonetics, Cambrex, Md.), which consists of keratinocyte basal medium (KBM-2) supplemented with KGM-2 SingleQuots. The cells were grown in an incubator at 37° C. in an atmosphere of 5% $CO_2$ and 95% air.

MTS cell viability assay. The toxic effect of the compounds on the cells was determined by calorimetric assay using a CellTiter 96 $AQ_{ueous}$ One Solution cell proliferation assay (MTS) kit (Promega, Wis.). MTS tetrazolium compound [3-(4,5-dimethylthiazol-2-yl)-5-(3-carboxymethoxyphenyl)-2-(4-sulfophenyl)-2Htetrazolium, inner salt] reduction is an indication of cell viability. Approximately 80% confluent cells were detached by treating with cell dissociate buffer and trypsin-EDTA solution. The cells were washed twice with trypsin neutralization solution (Clonetics) and resuspended in KGM at $2.5×10^5$ cells/ml. An aliquot (50 µl) of the cell solution was incubated with an equal volume of peptides or agent (12.5 to 200 µM) in a 96-well plate at 37° C. in a 5% CO2 atmosphere. After a 1.5-h exposure, 20 µl of MTS agent was added to each well, and the cells were further incubated at 37° C. in a 5% $CO_2$ atmosphere for 4 h. Absorbance at 490 nm was then measured using a microplate reader. Wells without drugs were used for cell viability, and wells without cells were used for blanking the spectrophotometer. Fifty percent inhibitory concentrations (IC50s) for each cell line were evaluated at a dose of drug causing 50% absorbance reduction in comparison to the untreated control cells.

Results

Candidacidal activity of peptides in saliva. First we determined the candidacidal activities (using *C. albicans* DIS isolate) of four peptides at different concentrations (25, 50 and 100 µM) in the clarified and unclarified whole human saliva (WHS) sample from one subject. It is important to point out that at these concentrations, the killing activities of all four peptides in 10 mM phosphate buffer (PB), pH 7.2, were 100% (results not shown). We determined previously, the ED50 for MUC7 12-mer-L, Hsn5 12-mer and Magainin-II are 2.1, 3.7 and 5.7 µM, respectively (4). The ED50 of MUC7 12-mer-D was determined in this study to be 2.6 µM (comparable to L-isomer, results not shown). As our results showed, much higher peptide concentrations were required for killing activity in saliva, especially in unclarified saliva (FIG. 1A-H, the first column of set of the 3 columns at each concentration of peptides). Even at 100 µM concentrations, Hsn5 12-mer showed no killing activity in unclarified saliva (FIG. 1F) and Magainin II in both salivas (FIG. G and H). On the other hand, MUC7 peptides, and in particular the D-isomer, showed considerable anticandidal activity in saliva. More specifically, at 100 µM concentration, in clarified saliva, MUC7 12-mer-D exhibited 94% activity (1C), compared to 57% exhibited by MUC7 12-mer-L (1A), 16% by Hsn5 12-mer (1E), and 0% by Magainin-II (1G). In the unclarified saliva, these peptides exhibited 64, 32, 0, and 0% killing, respectively. Thus, MUC7 12-mer-D was the most active peptide in both salivas.

Candidacidal activity of peptides in saliva supplemented with protease inhibitor cocktail (PIC) or EDTA. We expexted that addition of PIC to saliva will inhibit salivary proteases and the activity of the peptides will increase, with the exception of 10 MUC7 12-mer-D which should not be susceptible to degradation by proteolytic enzymes (designed to degrade only the natural L-amino acids). First, the amount of PIC added to saliva was optimized, so that the PIC alone had no or very low effect on the *C. albicans* cell viability (shown in FIG. 1 at 0 concentration of each peptide, as SL+PIC). In the presence of PIC, the activities of peptides increased at each concentration (FIG. 1, the second column at each concentration of peptides in the set of 3 columns). In terms of the PIC enhancement level, the Magainin-II activity was most enhanced, followed by Hsn5 12-mer and MUC7 12-mer-L. However, surprisingly, this activity increase happened even with MUC7 12-mer-D (FIGS. 1C and D), theoretically not susceptible to protease degradation. To investigate this phenomenon, we determined the effect of the EDTA alone at the same concentration as in the PIC cocktail (1 mM EDTA; final concentration was 0.5 mM) on the candidacidal activity of these four peptides. EDTA alone, as the PIC, had very little or no effect on *C. albicans* viability (shown in FIG. 1 at 0 concentration of peptides, as SL+EDTA). In the presence of peptides, and in clarified saliva, the EDTA alone achieved basically the same activity increase as the PIC (FIGS. 1A, C, E, and G). This indicated that in clarified saliva (bacteria were removed), the increase in the activity of peptides in the presence of PIC is mainly due to the chelating action of the EDTA, not due to the protease inhibition, and also why even the activity of MUC7 12-mer-D increased. On the other hand, in the unclarified saliva (FIGS. 1B, D, F and H), the activity of peptides in the presence of EDTA, with the exception of MUC7 12-mer-D, was lower than in the presence of the PIC.

Figure 2:
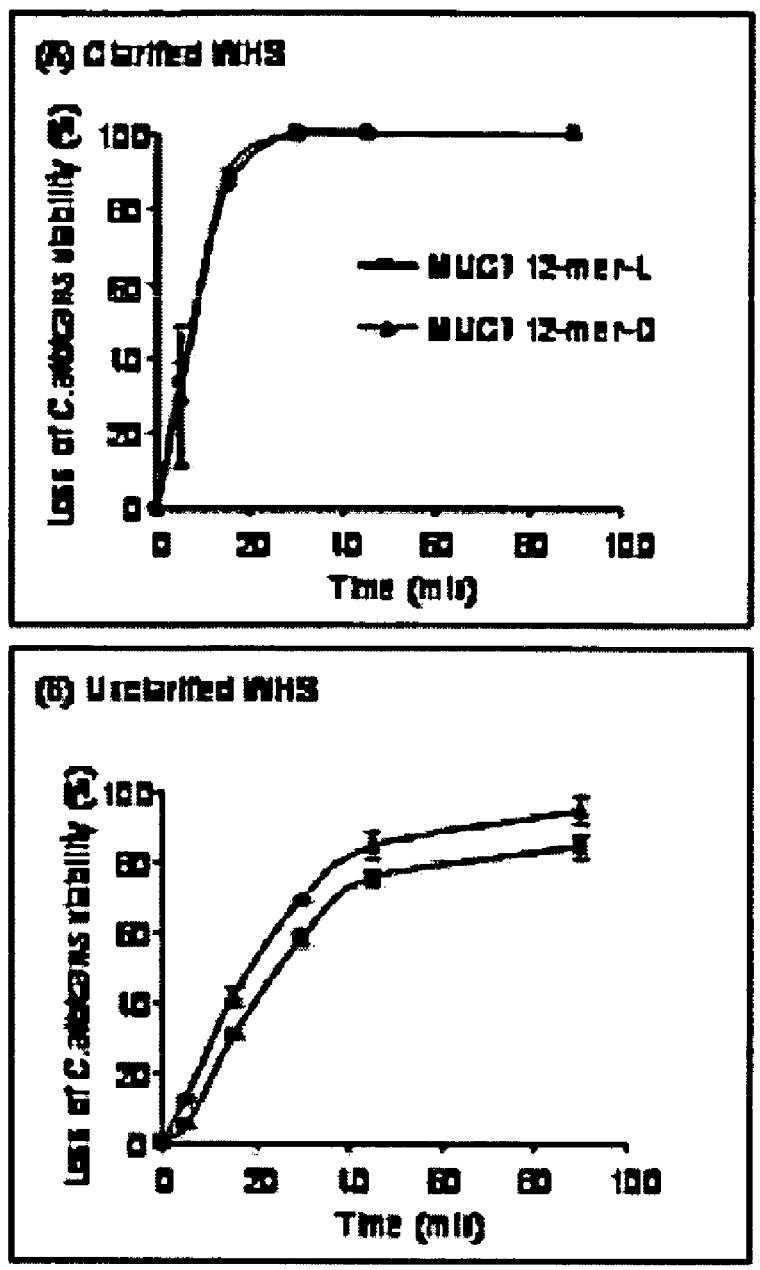
FIGS. 2(A) and (B). Time kinetics of MUC7 12-mers mediated killing. C. albicans cells (1×105 cells) were incubated with equal volume (20 µl, 50 µM final concentration) of MUC7 12-mer D (diamonds) and MUC7 12-mer-L (squares) in (A) clarified and (B) unclarified saliva containing PIC at 37° C. At indicated point in time, sample was diluted 20-fold with phosphate buffer (PB) and cell viability was determined by plating on SDA. Values represent the mean of three independent experiments, each of which was done in duplicate.

Time-dependent killing. In the next experiment we determined the kinetics of MUC7 12-mer-L and D killing. These experiments indicated that at concentration of 50 µM, both peptides exhibited similar killing curve pattern in clarified (FIG. 2A) and unclarified saliva (FIG. 2B). However, the peptides killed *C. albicans* faster in clarified than in unclarified saliva. In unclarified saliva, 90 min of incubation with MUC7 12-mer-L was needed to reach more than 80% killing of *C. albicans* (MUC7 12-mer-D showed slightly faster rate of killing that MUC7 12-mer-L in unclarified saliva). On the other hand in clarified saliva, the same percentage of killing was achieved in 20 min with both peptides.

Figure 3A:
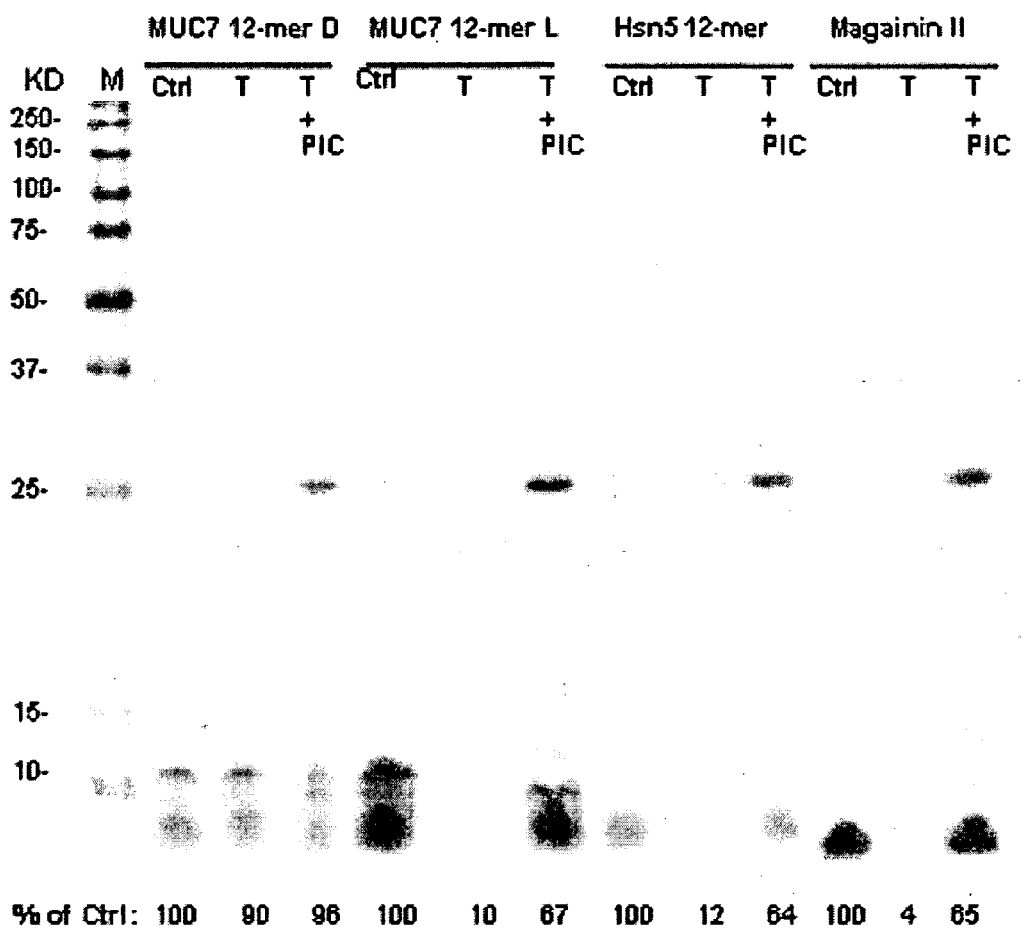
FIGS. 3A and 3B. Stability of antimicrobial peptides in (3A) Trypsin and (3B) unclarified saliva. Each peptide (3 µg in 5 µl of 0.5 M Tris-HCl buffer pH 7.5) was incubated with: 0.2 µg/ml trypsin containing PIC or no PIC for 0.5 h; or saliva (10 µl) for 1 h. The control of each compound was also incubated with Tris-HCl buffer in parallel. The samples were analyzed by 13% SDS-PAGE. The gel was stained with Coomassie brilliant blue and further analyzed for the peptide degradation by GS-700 Imaging Densitometer. The degradation was estimated by the equation: 1−(density of test band/density of control band)×100%. Ctrol: each peptide alone; T: trypsin plus peptide; T+PIC: trypsin containing PIC plus peptide; S: saliva plus peptide; S+PIC: saliva containing PIC plus peptide.
Figure 3B:
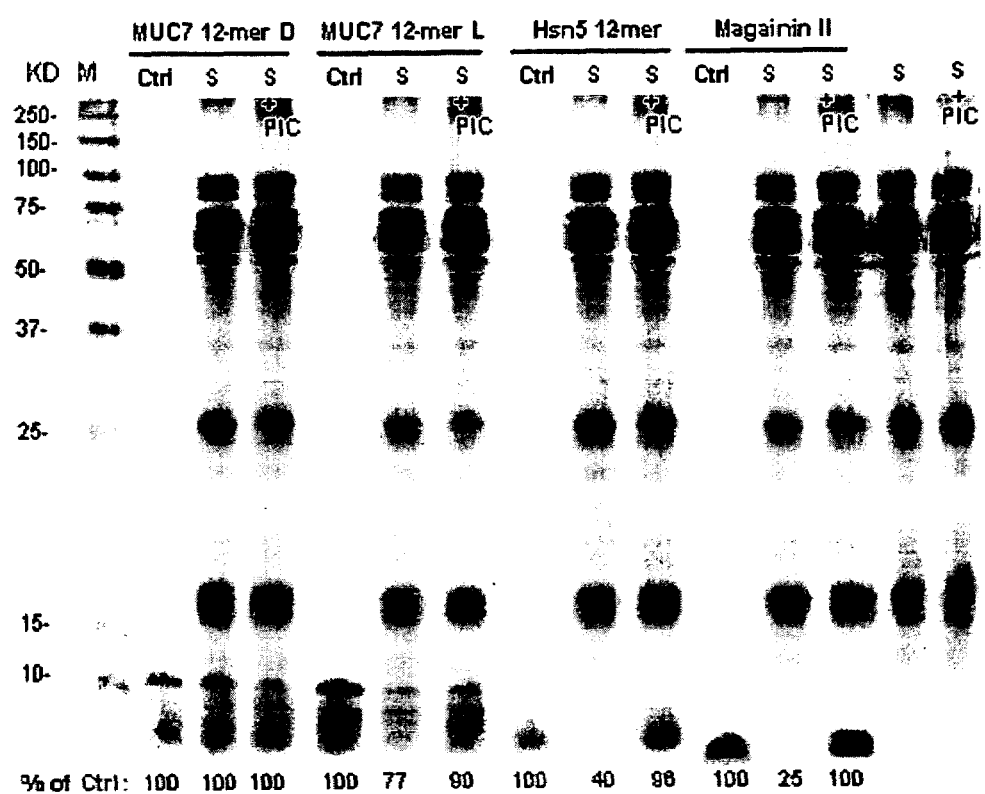
Figure 4:
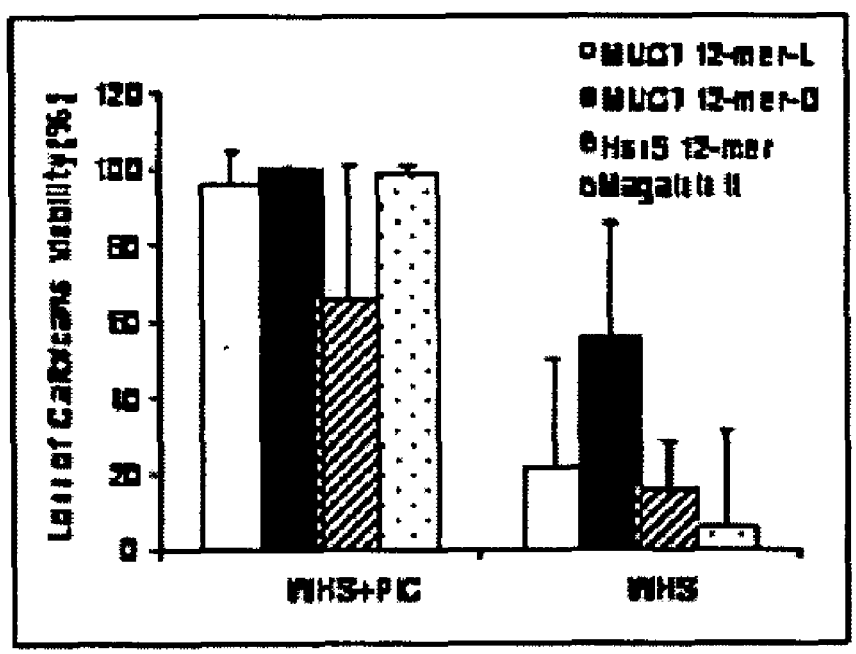
FIG. 4. PIC enhances the candidacidal activity of antimicrobial peptides in clarified WHS. Stimulated whole saliva was collected from 5 healthy subjects. Peptides (50 µM) were incubated with C. albicans cells (1×10$^5$) in the each individual saliva containing PIC (SL+PIC) at 37° C. for 1.5 hr and the loss of the cell viability was determined. Values represent the mean±S.D. (n=5). P<0.05 compared to the control without PIC (SL).

Peptide stability. The results of killing assays showed that the tested peptides (with the exception of MUC7 12-mer-D) are less active in unclarified then clarified saliva, probably due to degradation by salivary proteases. To confirm this, the peptide stability was determined in trypsin (FIG. 3A), unclarified saliva (FIG. 3B) and in clarified saliva (not shown), and degradation monitored by SDS-PAGE. FIG. 3B is a representative of several gels with whole unclarified saliva from different donors. The pattern of peptide degradation was similar with saliva from all donors. However, saliva of some individuals contains low molecular mass proteins/peptides that migrate at the same position as the antimicrobial peptides, interfering with the interpretation of results. Thus saliva of the donor showing no low molecular mass proteins was selected to illustrate the degradation patterns [FIG. 3B, the last 2 lanes, showing the protein profile of saliva (S) and saliva plus 12 PIC (S+PIC)]. As shown in FIGS. 3A and 3B, MUC7 12-mer-D is resistant to the degradation by both trypsin and saliva (lane T or S of MUC7 12-mer-D in gel A and B, respectively). The other three peptides, MUC7 12-mer-L, Hsn5 12-mer and Magainin-II, were degraded by trypsin (T lanes) as well as saliva (S lanes) although to a different degree. The degradation was determined quantitatively by GS-700 Imaging Densitometer and the percent of peptide remaining calculated. These values are indicated at the bottom of each well. For clarified saliva, similar pattern of degradation as in unclarified saliva was observed, however much less degradation occurred (results not shown). These results correlate well with the activity of the peptides in unclarified saliva, shown in FIG. 1, right panels. Candidacidal activity of peptides in saliva from different subjects. FIG. 4 shows the outcome of killing assay performed in clarified whole human saliva samples from 5 subjects. Considerable killing of C. albicans was observed when the fungal cells were exposed to each of the four peptides at concentration of 50 μM in the presence of PIC (from 60-100%), while the activities were 6 to 60% in the saliva without PIC. The difference is statistically significant ($p<0.05$). These results confirmed and extended the data presented in FIG. 1.

Activity of peptides in saliva against different candida strains. The in vitro candidacidal activities of MUC7 12-mer-L and D, Hsn5 12-mer, and Magainin-II against four Candida strains in clarified saliva are shown in Table 1. The data are presented as percent loss of cell viability compared to non-treated control. The following observations were made. For the three L peptides, each peptide tested exhibited low activity against all Candida strains in saliva without PIC; the activities were 0-20%, with the exception of 12-mer-L activity against both strains of C. albicans, showing 44~80% killing. In the presence of PIC, the activity values of MUC7 12-mer-L and of Magainin-II rose close to a 100% for all strains, but not that of Hsn5 peptide, which achieved the similar activity only against the C. albicans (ATCC strain). The activities against the other strains were much lower, in particular against both strains of C. glabrata (30-40%). On the other hand, MUC7 12-mer-D showed high activities against all strains tested even in saliva without PIC. Between 47-100% activity was observed with this peptide without PIC, and interestingly, it was very effective against both strains of C. glabrata (~100% killing). In conclusion, MUC7 12-mer-D was the most active peptide. This was true especially in saliva without PIC. It was followed by MUC7 12-mer-L. Hsn5 12-mer and Magainin-II showed basically no activity against C. glabrata and C. crusei and very low activity against C. albicans in saliva without PIC. These results again confirmed and extended the results presented in FIG. 1 and correlate well with the degradation patterns of the peptides in unclarified saliva, presented in FIG. 3B.

TABLE 1

| Strain | MUC7 12-mer-D | | MUC7 12-mer-L | | Hsn5 12-mer | | Magainin-II | |
|---|---|---|---|---|---|---|---|---|
| | PIC+ | PIC− | PIC+ | PIC− | PIC+ | PIC− | PIC+ | PIC− |
| C. albicans ATCC96112 | 100.00 ±0.00 | 74.24 ±35.67 | 98.90 ±1.32 | 79.93 ±31.18 | 97.17 ±2.21 | 19.07 ±29.92 | 97.90 ±0.76 | 7.17 ±5.25 |
| C. albicans DIS | 99.89 ±0.22 | 73.75 ±10.5 | 90.96 ±13.74 | 44.78 ±13.03 | 64.58 ±10.70 | 18.72 ±13.99 | 94.42± 3.78 | 0.00 ±0.00 |
| C. glabrata ATCC90030 | 99.80 ±0.28 | 100.00 ±0.00 | 94.20 ±0.30 | 20.60 ±1.70 | 30.60 ±15.60 | 1.70 ±1.50 | 99.06± 0.79 | 0.00 ±0.00 |
| C. glabrata 65C | 100.00 ±0.00 | 99.83 ±0.24 | 96.40 ±1.30 | 21.60 ±4.10 | 40.60 ±12.40 | 0.00 ±0.00 | 99.80± 0.29 | 0.00 ±0.00 |
| C. krusei | 98.86 ±0.00 | 47.16 ±8.84 | 99.50 ±0.02 | 17.59 ±13.53 | 74.43 ±29.49 | 0.00 ±0.00 | 100 ±0.00 | 0.00 ±0.00 |

Figure 5:
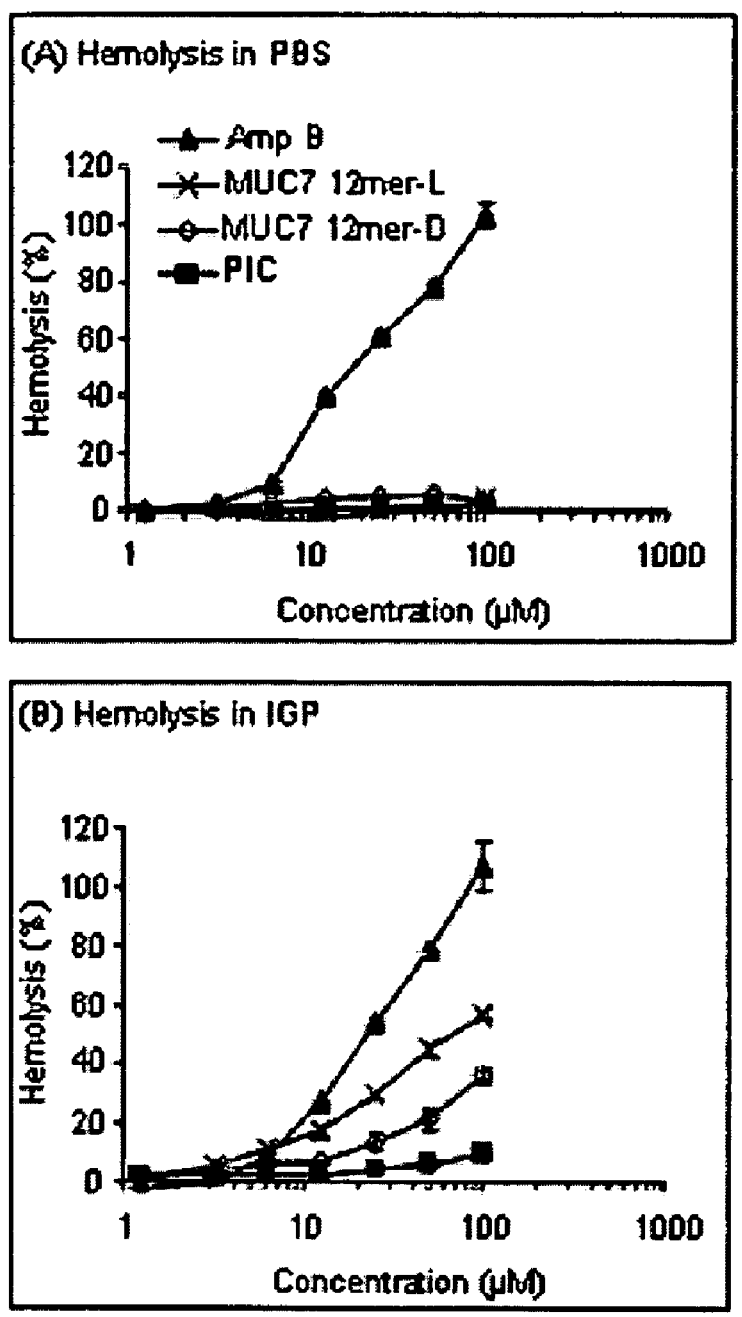
FIG. 5. Hemolysis of antifungal agents: amphotericin B (triangles), MUC7 12-mer-L (crosses), MUC7 12-mer-D (diamonds) and PIC (squares). Erythrocytes (final concentration 0.5%) were incubated for 1 h at 37° C. with a two-fold dilution series of peptides in PBS isotonic glucose phosphate (IGP) buffer. Hemolysis was determined by an absorbance reading of the supernatant at 450 nm and compared to hemolysis achieved with 1% Triton X-100 (reference for 100% hemolysis). Values represent the mean of two independent experiments, each of which was done in duplicate.

Toxicity of MUC7 12-mer-D. We determined the toxicity of MUC7 12-mer-D and PIC. As indicated in FIG. 5, they both showed relatively low hemolysis. Even at 100 μM concentration, MUC7 12-mer-D exhibited only 3.5% hemolysis in PBS (FIG. 5A) and 36% in IGP (FIG. 5B). These values are lower than that of MUC7 12-mer-L [4.3% in PBS, 56% in IGP (5)]. PIC exhibited 1.5% hemolysis in PBS (FIG. 5A) and 9.2% in IGP (FIG. 5B). Previously, we determined that Magainin-II exhibited 0% hemolysis in PBS, but 92% in IGP. Amphotericin-B showed 100% hemolysis in both buffers. Thus, MUC7 12-mer-D showed low toxicity compared to Magainin-II and Amphotericin-B (a compound widely used as antifungal therapeutic agent).

Figure 6:
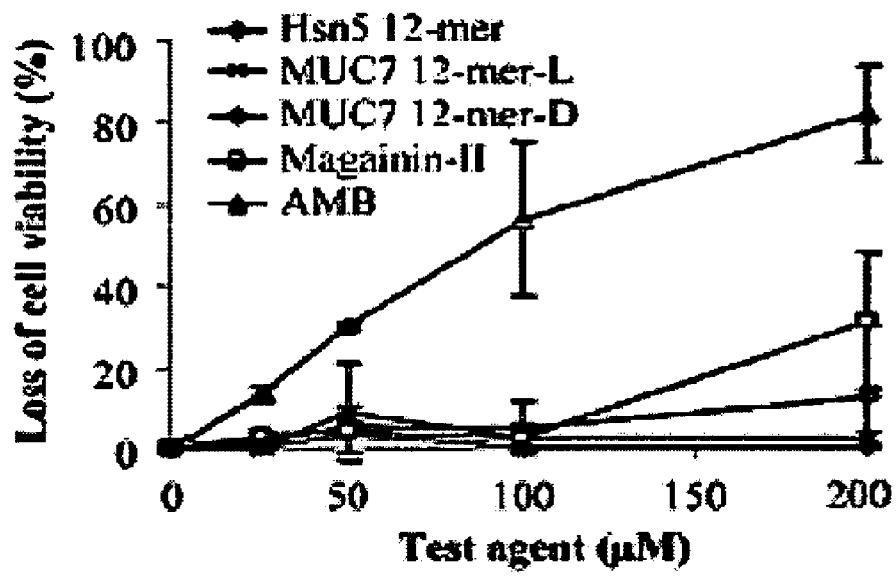
FIG. 6. Effect of peptides on viability of (A) HOK-16B cells and (B) KB cells. The toxic effect of the compounds on the cells was determined by calorimetric assay using a CellTiter 96 AQ$_{ueous}$ One Solution cell proliferation assay (MTS) kit, as described in the text. Briefly, the cells were grown to about 80% confluence, harvested, washed, resuspended in KGM, and dispensed into a 96-well microtiter plate. They were then exposed to different concentrations of peptides or amphotericin B at 37° C. and 5% CO$_2$ for 1.5 h. MTS agent was then added to each well, and the cells were further incubated for 4 h. Absorbance at 490 nm was then measured using a microplate reader. MTS reduction is an indication of cell viability. The viability is expressed as relative absorbance (percentage of no-agent control). Data represent the average and standard deviation of results from two independent experiments.
Figure 6:
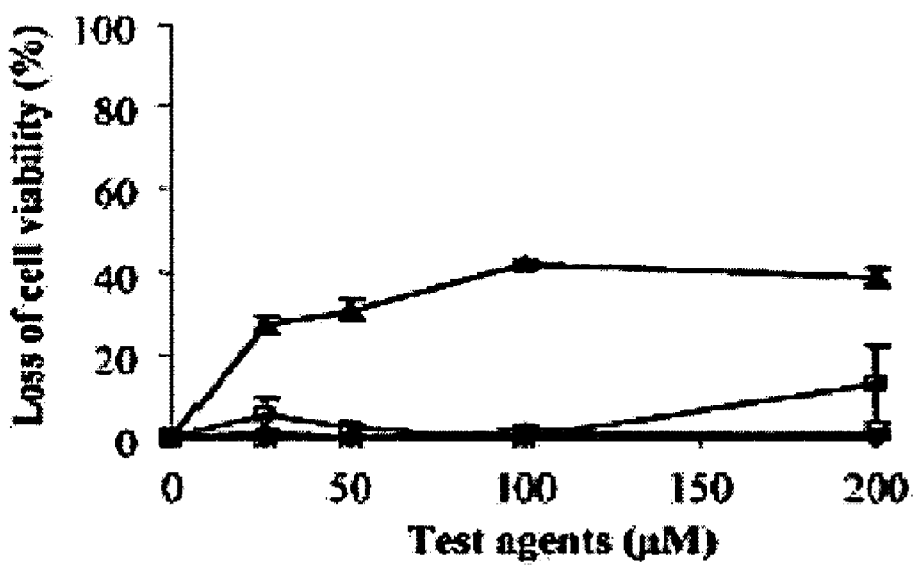

Cytotoxic activity against oral epithelial cells. HOK-16B and KB cells were used for the toxicity studies of the four peptides. The results depicted in FIG. 6 indicate that all peptides showed very low toxicity or no toxicity to these cell lines at all concentrations tested. Specifically, at the 100 μM concentration (the highest concentration used for candidacidal killing assays), the peptides showed no toxicity to either cell line. At the highest concentration tested (200 μM), none of these peptides caused 50% cytotoxic effect (IC50) against either cell line, but magainin-II caused about 30% loss of HOK-16B cell viability and MUC7 12-mer-D caused about 10%. Amphotericin B exhibited a dose-dependent toxic activity against HOK-16B, and the IC50 was 100 μM (FIG. 6A).

The longer half-life of D-isomers may actually be desirable particularly when these peptides are used for topical applications (e.g. oral or vaginal candidiasis infections).

EXAMPLE 2

This example demonstrates the in vivo antifungal efficacy of MUC7 12-mer peptides (L and D), in a murine oral candidiasis model (36) as compared to the activity of known antifungal agents, amphotericin B and clotrimazole, and the salivary peptide, Hsn5 12-mer. The efficacy of these peptides was compared for combating infection by C. albicans.

Materials and Methods

Materials

Tetracycline hydrochloride from Fort Dodge Animal Health, Fort Dodge, Iowa; Clotrimazole,(1-[o-chloro-a,a-diphenylbenzyl]-imidazole) and Amphotericin B from Spectrum Chemical Mfg Corp, Dardena, Calif.; Sabouraud Dextrose Agar, Brain Heart Infusion Agar and Bacto agar from Difco, Becton, Dickinson and Company, Sparks, Md.; Prednisolone, Chlorpromazine hydrochloride, Streptomycin sulfate and Protease Inhibitor Cocktail from Sigma-Aldrich, St. Louis, Mo.; Pluronic F127 from Gallipot Inc., Minn.; Calcium alginate swabs from Fischer Scientific, Fair Lawn, N.J.; Synthetic MUC7 12-mer (L and D) and Hsn5 12-mer (L) from Biosynthesis, Lewisville, Tex. C. albicans strain DIS was a clinical isolate from a patient with Denture Induced Stomatitis and was kindly provided by Dr. M. Edgerton, University at Buffalo, Buffalo, N.Y.; Mice ICR strain, Harlan Sprague Dawley, Indianapolis, Ind.

Methods

In Vitro Killing Assay

The assay was carried out as described previously (5). In brief, 20 µL of two-fold serial dilutions of MUC7 12-mer (L and D) and Hsn5 12-mer peptides (50 to 1.56 µM in deionized water) were incubated in duplicate with an equal volume (20 µL) of suspension of C. albicans ($1\times10^5$ cells/ml in 10 mM sodium phosphate buffer, pH 7.4). After incubation at 37° C. for 1.5 h, the reaction mixture was diluted 20-fold with sodium phosphate buffer, and aliquots (50 µL) plated on SDA plates. The number of colony-forming units (CFU) was counted. Percentage of killing was calculated as: [1–(amount of viable cells in the test group/amount of viable cells in the control group)]×100%.

C. albicans

For in vivo studies, C. albicans was grown in sabauraud dextrose broth in an orbital shaker at 37° C. Cells were harvested by centrifugation for 10 min at 3800×g (Beckman Model GS-15R Centrifuge). After washing three times in PBS, cells were resuspended in PBS to a final concentration of $2.5\times10^7$ cfu/ml.

Animals

Six to eight weeks old female ICR mice were used in this study. Animal experiments were performed in accordance with the guidelines for the care and use of animals approved by the IACUC, University at Buffalo, The State University of New York. Animals were kept in cages housing 4 to 5 mice and given ad libitum access to food and water. The photoperiods were adjusted to 12 h of light and 12 h of darkness daily.

Oral Candidiasis Model

A previously described protocol was adopted (14). The schedule for various procedures is presented in Table 2. Mice were immunosuppressed with two subcutaneous injections of prednisolone at a dose of 100 mg/kg body weight 1 day prior to and 3 days after the infection with C. albicans. Tetracycline hydrochloride in drinking water at a concentration of 0.83 mg/ml was given to mice beginning 1 day before infection. Mice were anesthetized by intramuscular injection with 60 µl of 2 mg/ml chlorpromazine chloride, using a dose of 10 mg/kg body weight of mice. While under anesthesia, a small cotton ball soaked in 0.1 ml aliquot of C. albicans cell suspension ($2.5\times10^6$ cells) was used to swab the entire oral cavity of the anesthetized mice.

TABLE 2

Experimental protocol for the in vivo study

| Day | Procedure |
|---|---|
| −1 | Drinking water supplemented with tetracycline hydrochloride. Immunosupression with prednisolone s/c. |
| 0 | Oral cavity of mice were infected with C. albicans. Mice sedated for 3 h using IM injection with chlorpromazine chloride (2 mg/ml). |
| 3 | Initial microbiological evaluation: tongue examination and fungal burden determination. Immunosuppressant (prednisolone) re-administered. |
| 4 | Antifungal agent application started. Mice received antifungal agent and placebo drug according to the treatment group they belonged. |
| 5-9 | Treatment continued for 6 days. |
| 7 and 10 | Microbiological evaluation at day 3 and day 6 post-treatment. |
| 10 | Tongue excised for histopathological evaluation. |

Evaluation of Infection

Visual evaluation was done by carefully extending the tongue of randomly picked mice using blunt-end forceps, while the mice were under isoflurane sedation. Presence of thick, white curd-like patches indicated candidal infection. At day 3 post-infection, all animals were examined for evidence oral candidal infection by microbiological evaluation. The entire oral cavity of anesthetized mice was swabbed using a sterile calcium alginate disposable swab (Fisher Scientific), dampened with sterile PBS. Cells were then released from the swab into 1 ml PBS. Serial 10-fold dilutions were plated on SDA plates supplemented with streptomycin (30 µg/ml). Plates were incubated for 24 h at 37° C. and yeast cell count expressed as $\log_{10}$ of cfu/ml.

Histopathological Examination

Tongues from sacrificed animals were used for histological studies. They were fixed in 10% formalin and embedded in paraffin. Serial five-µm sections were cut from the paraffin block and stained with periodic acid-Schiff (PAS) reagent for detection of C. albicans.

Antifungal Treatment

Mice were randomly divided into various treatment groups with 8 mice per group. Antifungal agents were employed on an equimolar basis, and included amphotericin B (1.75%), clotrimazole (0.66%), MUC7 12-mer (RKSYK-CLHKRCR—SEQ ID NO:1) (L; 3%), MUC7 12-mer (D; 3%), MUC7 12-mer (D; 3%) containing $Na_2EDTA$ (1 mM), MUC7 12-mer (L; 3%) containing protease inhibitor cocktail (PIC) (1%), and Hsn5 12-mer (AKRHHGYKRKFH—SEQ ID NO:2) (3%). They were all emulsified in Pluronic F127, (20% lipoil), a polymer of polyoxyethylene and polyoxypropylene (non-ionic surfactant). Animals were anesthetized using isoflurane; while sedated, about 30 to 40 µl of the antifungal emulsion was applied on the tongue and spread throughout oral cavity. The treated mice were under sedation for additional 5 min under isoflurane. Animals were not given access to food and water for 1 h following the application.

Treatment Evaluation

Fungal burden was re-evaluated quantitatively after 3 and 6 days of treatment, using the same technique as the one used for initial evaluation. Randomly picked mice from each group was subjected to histopathological evaluation, after 6 days of treatment. Blood from randomly sacrificed mice from each treatment group was analyzed for any changes in the serum liver (AST, ALT, ALP etc.) and kidney enzymes (BUN, glucose, creatinine etc) levels.

Statistical Analysis

Statistical analysis was performed using a significance level set at 0.05 ($\alpha$) and a significant group size (n=8). Initial infection and antifungal treatment efficacy were determined using analysis of variance (ANOVA), expressed as $\log_{10}$ cfu, and Scheffe's multiple comparison test was used to determine the differences between various treatment groups.

Results

In Vitro Study

The in vitro susceptibility of *C. albicans* to MUC7 12-mer (L and D), and Hsn5 12-mer was tested using killing assay (cells in solution phase). The $ED_{90}$ or concentration required to kill 90% cells for MUC7 12-mer L, D and Hsn5 12-mer was 4.79, 1.56 and 12.5 µM, respectively.

Induction of Oral Candidiasis

Figure 7:
FIG. 7. Macroscopic examination of tongue: C. albicans infection was induced by swabbing the oral cavity of mice with a cotton ball soaked in a C. albicans cell suspension. On the 3rd day, tongue was examined for the presence of white curd-like patches. A, healthy (control) tongue; B, tongue infected with C. albicans.
Figure 7:
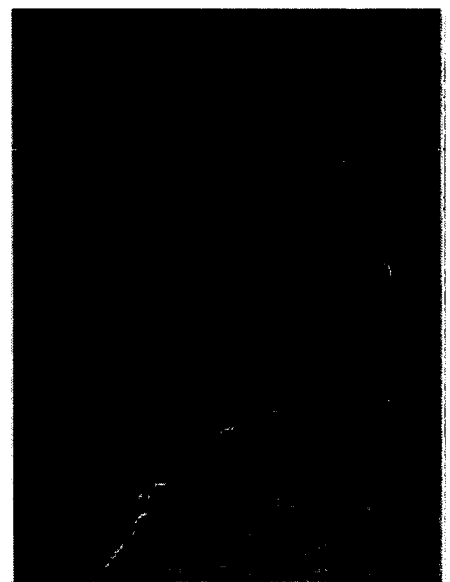

Visual examination of the mice tongue revealed the presence thick, white curd-like patches, similar to the clinical appearance of oral thrush in humans. A representative is presented in FIG. 7. Microbiological evaluation confirmed the induction of infection. The CFUs were in the range, $\log_{10}$ 4.1 to $\log_{10}$ 4.52 (Table 3) indicating consistency of infection in various mice.

Therapeutic Efficacy of Antifungal Agents in Oral Candidiasis Model

Infection was effectively established in all animals and the fungal burden reached comparable levels with no statistically significant difference among groups (p=0.36). Antifungal treatment was performed for 6 consecutive days starting on the 4$^{th}$ day post-infection. Comparing to the placebo, at days 3 and 6 post-treatment, amphotericin B and clotrimazole were effective in diminishing the infection, as evident from the decrease in log cfus (Table 3) and this is statistically significant (p<0.05) (Table 3). Effects of MUC7 12-mer peptide, L and D forms, as well as these peptides plus additives (PIC and EDTA), were not statistically significant on day 3 post-treatment (p>0.05). However, by the end of the treatment period, compared to the placebo, fungal burden in the MUC7 peptide-treated mice were drastically reduced and showed statistically significant differences (p<0.05). In the experimental study II, Hsn5 12-mer, a known salivary antifungal peptide, was also examined along with MUC7 12-mer. Compared to the placebo, its effect at days 3 and 6 post-treatment was not statistically significant (p>0.05). However, we have also observed a reduction in fungal burden in placebo mice, contrary to the observations of the first study. The antifungal effects of MUC7 12-mer (L) peptide and amphotericin B were still (statistically) significantly different from the placebo.

TABLE 3

| Treatment | Log10 cfu/ml (Mean +S.D.) | | |
|---|---|---|---|
| | Initial infection | 3-days treatment | 6-days treatment |
| Experimental study I | | | |
| Placebo | 4.44 ± 0.27 | 3.60 ± 0.37 | 3.11 ± 0.61 |
| Amphotericin B | 4.52 ± 0.15 | 1.79 ± 1.16* | 0.75 ± 1.04* |
| Clotrimazole | 4.50 ± 0.20 | 1.58 ± 1.36* | 0.53 ± 0.99* |
| MUC7 12-mer (L) | 4.09 ± 0.49 | 2.26 ± 1.10 | 0.67 ± 0.93* |
| MUC7 12-mer (D) | 4.20 ± 0.30 | 2.78 ± 0.43 | 1.04 ± 1.14* |
| MUC7 12-mer (L) +PIC | 4.15 ± 0.36 | 2.46 ± 0.68 | 0.73 ± 1.02* |
| MUC7 12-mer (D) +Na$_2$EDTA | 4.21 ± 0.39 | 2.76 ± 0.53 | 0.89 ± 1.24* |
| Experimental study II | | | |
| Placebo | 4.25 ± 0.45 | 3.19 ± 0.72 | 1.49 ± 1.26 |
| MUC7 12-mer (L) | 4.26 ± 0.43 | 2.28 ± 1.11 | ND |
| Amphotericin B | 4.26 ± 0.54 | 1.23 ± 1.44* | ND |
| Histatin 5 12-mer | 4.28 ± 0.37 | 2.19 ± 1.07 | 0.82 ± 1.18 |

*Statistically significant difference
ND—Not detected

Figure 8:
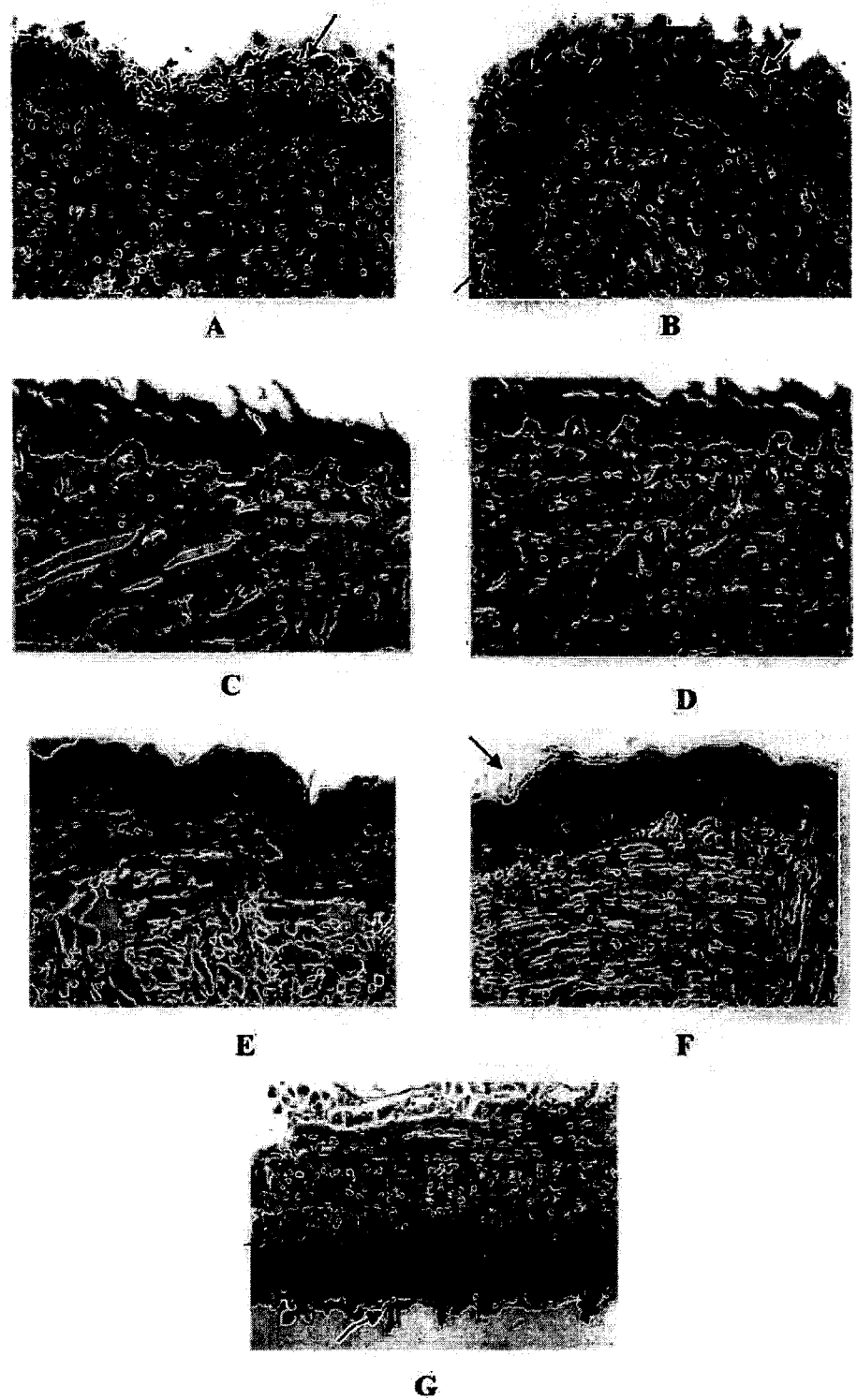
FIG. 8. Histopathological examination of tongue sections: PAS staining was used. Tissue section from infected untreated control (A) shows C. albicans infiltrating the stratum corneum (black arrow). Infected untreated control tissue is shown to provide histological evidence of the ability of C. albicans (DIS) to colonize the oral mucosa. This represents the external control and is comparable to but slightly higher than placebo treated mouse tissue (B). Clotrimazole, amphotericin B and MUC7 12-mer (L) treated tissue sections (C, D and E) show healthy tissues with absence of visible candida microorganisms. On the other hand, MUC7 12-mer (D) and Hsn5 12-mer (L) treated tissue sections (F and G) (black arrows) show fewer microorganisms, along with acanthosis of the stratum spinosum in the Hsn5 12-mer sample (F) (red arrow). Tissues, A to G: 20× magnification.

Histopathological sections of tongues presented in FIG. 8 indicate that after 7 days of treatment, amphotericin B, clotrimazole and MUC7 12-mer (L) treated mice shows healthy tissue and absence of visible microorganisms (FIGS. 8C, 8D and 8E). On the other hand, tissue from placebo treated mice shows the presence and infiltration of stratum corneum by *C. albicans* (FIG. 8B). Tissue sections from Hsn5 12-mer and MUC7 12-mer (D) treated mice shows the presence of fewer cells, compared to the placebo (FIGS. 8F and 8G). In addition, the tissue section from Hsn5 12-mer treated mice also showed acanthosis of the stratum spinosum (FIG. 7G). Tissues from all infected and treated animals were compared to the tissue from infected untreated mouse, which served as an external control, and showed numerous *C. albicans* infiltrating the epithelium even at the end of study period (FIG. 8A).

Results of the serum liver and kidney enzyme level analysis indicated that overall, none of the antifungal agents used for the in vivo studies significantly affected the enzyme levels.

EXAMPLE 4

This example demonstrates the effectiveness of MUC7 12-mer-D and MUC7 12-mer-L in inhibiting or preventing the formation of oral biofilm. To illustrate this embodiment, we examined the effect of these peptides on the formation and eradication of *S. mutans* biofilm.

Materials and Methods

Peptides and Chemicals

MUC7 12-mer-L (RKSYKCLHKRCR—SEQ ID NO:1, aa 40-51 of the parent MUC7), MUC7-12-mer-D (D amino acid isomer), MUC7-20-mer (LAHQKPFIRKSYKCLH-KRCR—SEQ ID NO:4, aa 32-51 of the parent human salivary mucin, MUC7), Hsn5 12-mer (AKRHH-GYKRKFH, aa 4-15 of the parent Hsn5), and Magainin-II (GIGKFLHSAKKFGKAFVGEIMNS (SEQ ID NO:3), 24 aa peptide from frog skin) were custom-synthesized by Bio-Synthesis (Lewisville, Tex.). The company analyzed the prepared peptides by HPLC and mass spectrometry. The purity (>70%) was taken into consideration in preparation of the stock solution of each peptide for antifungal assays. The peptides were dissolved in sterile dd-water at 1 mg/mL; aliquots were freeze-dried and stored at −20° C. For each experiment, the freeze-dried peptides were re-dissolved at 1 mg/mL in sterile dd-water. Chlorhexidine digluconate solution (Sigma Chemical Co., St. Louis, Mo.) was diluted to 0.04 mg/ml with sterile dd-water.

Bacterial Strains and Growth Media

The bacteria used in this study included *Streptococcus mutans* ATCC10449, *Streptococcus mutans* AU 159, *Streptococcus mutans* GS-5, *Streptococcus mutans* GS-5 mutant (^gtf BCD), *Streptococcus gordonii* Challis, *Porphyromonas gingivalis* W50, *Porphyromonas gingivalis* 381, *A. actinomycetemcomitans* NCTC 9710, *Pseudomonas aeruginosa* ATCC 17648, and *Escherichia coli* HB101. One quarter strength (25%) of brain heart infusion broth (BHI, DIFCO Laboratories, Detroit, Mich.) was used for the growth of *S. mutans*, *S. gordonii*, *A. actinomycetemcomitans*, *Ps. aeruginosa*, and *E. coli*. For growth of *P. gingivalis*, tryptic soy broth-yeast extract medium (TSBY, DIFCO Laboratories, Detroit, Mich.) supplemented with cysteine hydrochloride (0.05%), menadione (0.02 µg/ml), hemin (5 µg/ml), and potassium nitrate (0.02%) was used. All bacteria were cultured at 37° C.; *Ps. aeruginosa* and *E. coli* were grown aerobically, and the other bacteria, anaerobically. To prepare bacterial cell suspension for antibacterial activity assays, each overnight culture was harvested by centrifuge (3783 g, 10 min), washed once with 10 mM sodium phosphate-buffered saline (PBS, pH 7.2), resuspended in PBS and adjusted to a concentration of $1\times10^6$ cells/mL.

Bacterial Susceptibility Assay

MICs of the peptides were determined by broth microdilution method as previously described (5). Briefly, two-fold serial dilutions of each peptide were prepared with 25% BHI medium at a volume of 200 µl per well in 96-well flat-bottom microtiter plates (Costar, Cambridge, Mass.). The final concentration of the peptides ranged from 0.78 to 100 µM, and chlorhexidine (CHX), used as a positive control, from 20 to 0.16 µM (10 to 0.078 µg/mL). The microtiter plate was inoculated with bacterial cell suspension with final concentration of $5\times10^6$ CFU/mL for *P. gingivalis* and $5\times10^5$ CFU/mL for the other bacterial species. After incubation at 37° C. for 48 h, the absorbance was measured at 595 nm by using a microplate reader (Model 3550, Bio-Rad, Japan) to assess the cell growth. The MIC endpoint was defined as the lowest concentration of the test agent that completely inhibited growth, or produced at least 90% reduction in absorbance compared with that of the drug-free control. The MIC value represents the median of at least three independent experiments. The minimal bactericidal concentration (MBC) was determined as follows. Aliquot (100 µl) of cell suspension was taken from two wells above MIC, centrifuged, and washed three times with PBS. Then each cell suspension was plated on TSBY agar plate, and bacterial cells were enumerated after incubation at 37° C. for 48 h. The MBC was defined as the lowest concentration of the peptide at which more than 99.9% of cells were killed compared to non-treated control.

Growth Curve Assay

The effect of the peptides on the growth of the *S. mutans* was performed. A bacterial culture was grown in 25% BHI at 37° C. to OD at 600 nm of 0.1 and then equally allocated into 50-ml tubes. Each peptide was added to the cultures to final concentrations of 25, 12.5, and 6.25 µM (2×MIC, 1×MIC, and ½×MIC, respectively). Culture without peptide was used as a bacterial growth control. The culture was grown for 10 h and the absorbance at 600 nm of the aliquot (1 ml) was recorded at 1 h interval.

Time-Kill Assays

For the peptides MUC7 12-mer-L, MUC7 12-mer-D, and MUC7 20-mer, time-kill kinetic studies against *S. mutans* were performed by the broth macrodilution method. *S. mutans* GS-5 ($1\times10^6$ CFU/ml) and antibacterial agens (find concentrations of 12.5 µM for each peptide, and 2 µM for CHX; their MICs) were incubated in 25% BHI at 37° C. At the time of 0, 1, 2, 4, 8, and 24 h, samples were taken and viable counts determined as follows: The samples were serially diluted ($10^{-1}$ to $10^{-4}$) in sterile 10 mM PBS (pH 7.2) and 50 µl aliquots were plated onto TSBY agar. The plates were incubated anaerobically at 37° C. for 48 h, followed by enumerating the CFU. Killing curves were constructed by plotting the $\log_{10}$ CFU per milliliter versus time over 24 h. All assays were done in duplicate on at least two occasions.

Biofilm Susceptibility Assay

The effect of the peptides on *S. mutans* in biofilm formation was examined by the microdilution method. This method is similar to the MIC assay for planktonic cells. Two-fold serial dilutions of each peptide were prepared in wells of polystyrene microtiter plates (Microtest tissue culture plate, 96 well, Falcon, Becton Dickinson and Company, N.J.) containing 25% BHI medium supplemented with 1% sucrose (BHIS) at a volume of 200 µl per well. The final concentration of the peptide ranged from 0.78 to 100 µM for each peptide. Chlorhexidine (CHX, 0.078 to 10 µg/mL) was used as the positive control, the medium without drug as the non-treated control, and the medium alone as the blank control. The cells suspension of *S. mutans* GS-5 was prepared as describe in MIC assay and 20 µl aliquot (final concentration of cells $5\times10^5$ CFU/mL) was inoculated to the wells of polystyrene microtiter plates. After incubation at 37° C. for 20 h, the culture supernatants from each well were decanted and planktonic cells were removed by washing with PBS, pH 7.2. The biofilm was fixed with methanol for 15 min and then air dried at room temperature. The biofilm was then stained with 0.1% (wt/vol) crystal violet (Sigma) for 5 min. and rinsed thoroughly with water until the control wells appeared colorless. Biofilm formation was quantified by the addition of 200 µl of 95% ethanol to each crystal violet-stained well. The plate was rocked at room temperature for 30 min and the absorbance at 595 nm ($A_{595\ nm}$) was determined with a microplate reader (BioRad Model 3550 Microplate Reader). Percentage of inhibition was calculated with the equation: (1−$A_{595}$ nm of the test/$A_{595nm}$ of non-treated control)×100. Minimum biofilm inhibition concentration (MBIC$_{50}$) was defined as the lowest agent concentration that showed 50% or more inhibition on the formation of biofilm.

To examine the effects of the peptides on 1-day mature biofilm, *S. mutans* GS-5 was inoculated into the wells of another polystyrene microtiter plate containing BHIS at a volume of 200 µl per well. After incubation at 37° C. for 24 h, the culture supernatants from each well were decanted and planktonic cells were removed by washing with PBS. BHIS containing 0.78 to 100 µM peptides, prepared in another microtiter plate, was then transferred to the 1-day biofilm plate, and further incubated at 37° C. for one day. The biofilm was fixed, stained, and quantified as describe above. Minimum biofilm eradication concentration (MBEC$_{50}$) was defined as the lowest drug concentration that showed 50% or more eradication of biofilm.

Results

MIC and MBC

The concentration of the peptides required to inhibit and to kill planktonic bacteria (MIC and MBC) are summarized in Table 4. Among the test bacterial species, *S. mutans* was most susceptible to the peptides, followed by *E. coli*, *S. gordonii*, *A. actinomycetemcomitans*, *P. gingivalis*, and *Ps. aeruginosa*. MUC7 peptides (12-mer-L, 12-mer-D, and 20-mer) exerted 2 fold higher antibacterial activities against *S. mutans* (MICs of 12.5 µM) than Hsn5-12-mer and Magainin-II (MICs of 25 µM). The MBC values of MUC7 peptides (12-mer-L, 12-mer-D, and 20-mer), as well as chlorhexidine against *S. mutans* were equal to their corresponding MIC, indicating that MUC7 peptides, similar to the control agent chlorhexidine exerted bactericidal rather than bacteriostatic activity against *S. mutans*.

MUC7 20-mer (12.5 µM or 31.4 µg/ml) showed the fastest killing rate for *S. mutans*, followed by MUC7 12-L and D (12.5 µM or 19.7 µg/ml). Hsn5 12-mer (25 µM or 39.5 µg/ml) or positive control agent chlorhexidine (2 µM or 1.3 µg/ml) showed slow killing rate compared to the other agents. After 4 h incubation, Magainin II, MUC7 20-mer, MUC7 12-mer-L, MUC7 12-mer-D, Hsn5 12-mer, and chlorhexidine reduced the viable counts of *S. mutans* by 3, 2, 2, 2, 1, and 1 $\log_{10}$, respectively.

Biofilm Inhibition

Figure 11:
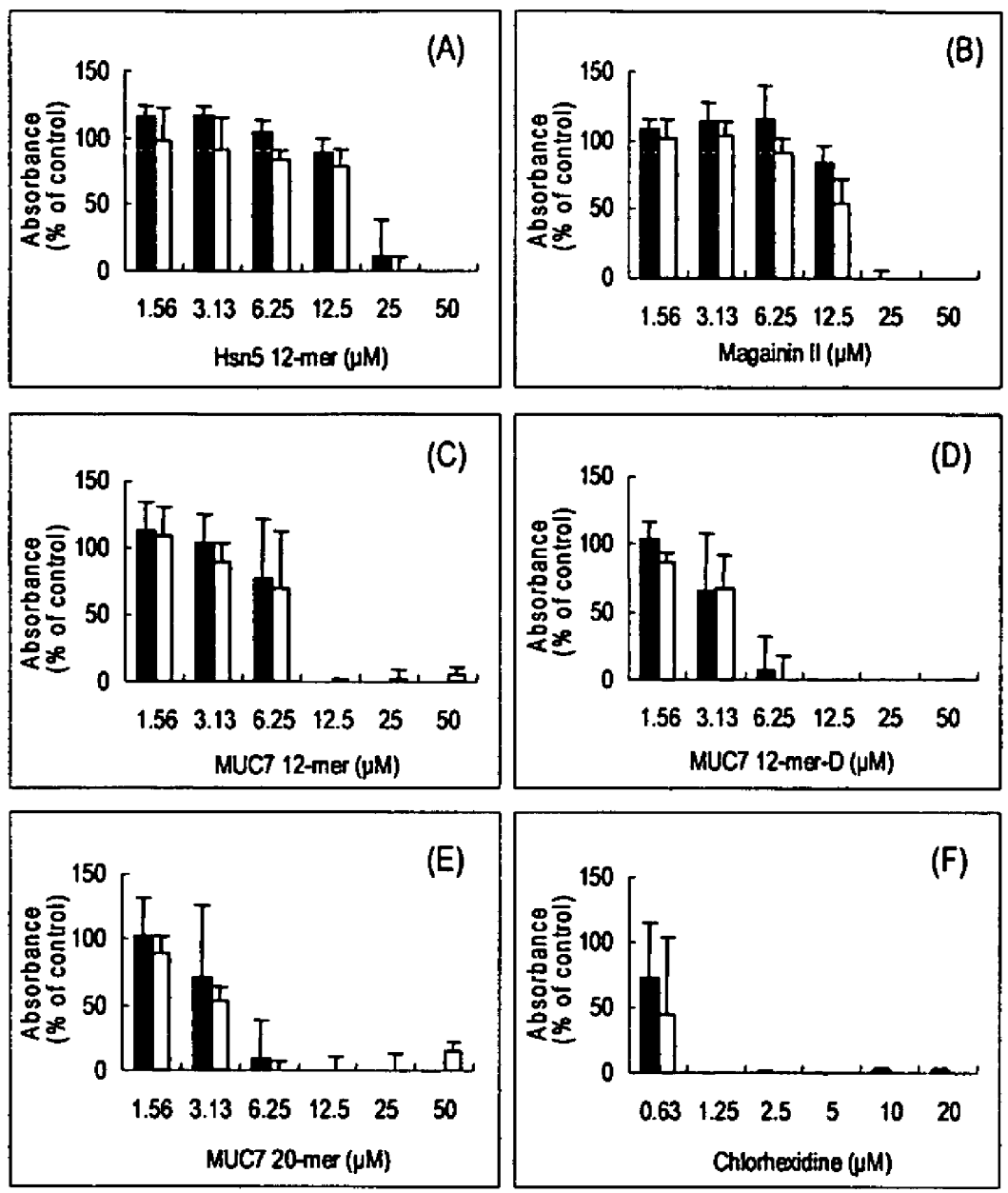
FIG. 11. Effect of peptides on the biofilm formation of S. mutans. The bacterial cells (5×10$^5$ cfu ml$^{-1}$) were inoculated in 96-well microtiter plate containing 25% BHIS medium with different concentration of each agent. Culture without agent was used as no treatment control. After incubation at 37° C. for 24 h, absorbance at 595 nm was recorded to assess the cell growth. Biofilm assay was performed by discarding the supernatants, washing with PBS, fixing with methanol, and staining with CV. The absorbance at 570 nm was recorded to assess the amount of biofilm. The activity was expressed as % of control. Data represents mean and SD of two independent tests with duplicates for each. Empty bar: growth, solid bar: biofilm.

MUC7 peptides exhibited an inhibitory effect on the formation of *S. mutans* biofilm with $MBIC_{50}$ from 12.5 to 50 µM, and eradication activity against developed 1-day *S. mutans* biofilm with $MBEC_{50}$ from 25 to >50 µM, (2 to 4 fold higher than the MIC of the planktonic cells). Consistent with the activity against planktonic bacterial cells, MUC7 peptides showed 2 fold higher activities against *S. mutans* biofilm than Hsn 5 12-mer or Magainin II (Table 5 and FIG. 11).

TABLE 4

| Species | Strain | Test agent | MIC (µM) | MIC (µg/ml) | MBC (µM) | MBC (µg/ml) |
|---|---|---|---|---|---|---|
| *S. mutans* | GS-5 | MUC7 12-mer-L | 12.5 | 19.7 | 12.5 | 19.7 |
| | GS-5-gtfBCD | MUC7 12-mer-D | 12.5 | 19.7 | 12.5 | 19.7 |
| | AU 159 | MUC7 20-mer | 12.5 | 31.4 | 12.5 | 31.4 |
| | ATCC10449 | Hsn5 12-mer | 25.0 | 39.5 | 50.0 | 79.0 |
| | | Magainin II | 25.0 | 61.7 | 50.0 | 123.5 |
| | | Chlorhexidine | 2.5 | 1.2 | 2.5 | 1.2 |
| *S. gordonii* | Challis | MUC7 12-mer-L | 50.0 | 79.0 | 100.0 | 158.0 |
| | | MUC7 12-mer-D | 50.0 | 79.0 | 100.0 | 158.0 |
| | | MUC7 20-mer | 12.5 | 31.4 | 25.0 | 62.8 |
| | | Hsn5 12-mer | >100 | >158 | >100 | >158 |
| | | Magainin II | 50.0 | 123.5 | >50 | >123 |
| | | Chlorhexidine | 2.5 | 1.2 | 4.0 | 2.0 |
| *A. actinomycetemcomitans* | NCTC 9710 | MUC7 12-mer-L | >100 | >158 | >100 | >158 |
| | | MUC7 12-mer-D | >100 | >158 | >100 | >158 |
| | | MUC7 20-mer | 100.0 | 251.3 | 100.0 | 251.3 |
| | | Hsn5 12-mer | >100 | >158 | >100 | >158 |
| | | Magainin II | 50.0 | 123.5 | 50.0 | 123.5 |
| | | Chlorhexidine | 20.0 | 10.1 | 20.0 | 10.1 |
| *P. gingivalis* | W 50 | MUC7 12-mer-L | >100 | >158 | ND | ND |
| | 381 | MUC7 12-mer-D | 50.0 | 79.0 | 100.0 | 79.0 |
| | | MUC7 20-mer | >100 | >251 | ND | ND |
| | | Hsn5 12-mer | >100 | >158 | ND | ND |
| | | Magainin II | >100 | >246.9 | ND | ND |
| | | Chlorhexidine | 2.5 | 1.2 | 2.5 | 1.3 |
| *Ps. aeruginosa* | ATCC 17648 | MUC7 12-mer-L | >100 | >158 | >100 | >158 |
| | | MUC7 12-mer-D | 100.0 | 158.0 | >100 | >158 |
| | | MUC7 20-mer | >100 | >251 | >100 | >251 |
| | | Hsn5 12-mer | >100 | >158 | >100 | >158 |
| | | Magainin II | >100 | >246.9 | 100.0 | 246.9 |
| | | Chlorhexidine | 10.0 | 5.1 | 10.0 | 5.1 |
| *E. coli* | HB101 | MUC7 12-mer-L | 25.0 | 39.5 | 25.0 | 39.5 |
| | | MUC7 12-mer-D | 12.5 | 19.7 | 12.5 | 19.7 |
| | | MUC7 20-mer | 100.0 | 251.3 | 100.0 | 251.3 |
| | | Hsn5 12-mer | 100.0 | 158.0 | 100.0 | 158.0 |
| | | Magainin II | 12.5 | 30.9 | 12.5 | 30.9 |
| | | Chlorhexidine | 2.5 | 1.3 | 2.5 | 1.3 |

Figure 9:
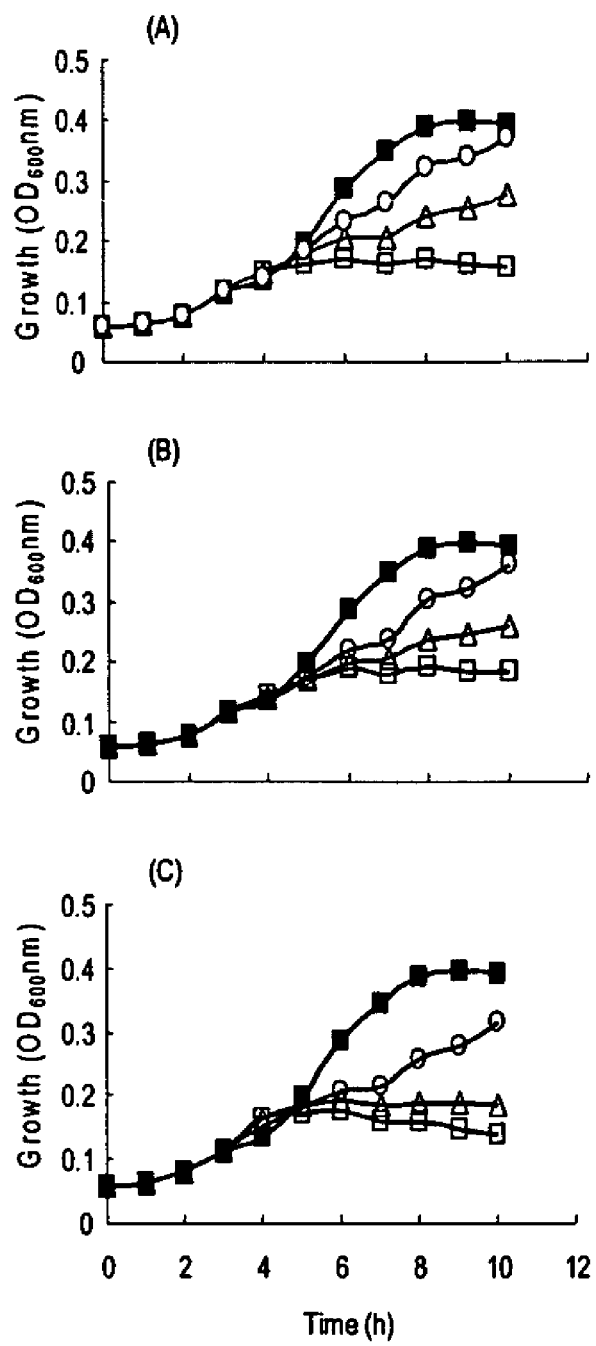
FIG. 9. Effect of peptides on the growth of S. mutans. S. mutans GS-5 was grown in 25% brain heart infusion (BHI) broth at 37° C. to OD 600 nm of 0.1, then equally allocated into 50-ml tubes. After addition of each peptide, the culture was grown for 10 h and the absorbance at 600 nm was recorded at 1 h interval. The data represents one of three independent experiments. Concentrations of peptide: 2×MIC, 25 µM (○), MIC, 12.5 µM (Δ), and ½ MIC, 6.25 µM (□), culture without peptide was used as non-treatment control (■).

*Four *S. mutans* strains and two *P. gingivalis* strains were tested and the MIC and MBC values represent median of the observations Growth Inhibition and Time-Kill FIG. 9 shows the effect of peptides on the growth of *S. mutans*. MUC7 peptides exerted inhibition on exponentially growing *S. mutans* in a dose-dependent manner. Upon addition of the peptides, cells continued to grow at the same rate for approximately 1 h. A decrease in bacterial growth rate was observed after further exposure to the peptide.

Figure 10:
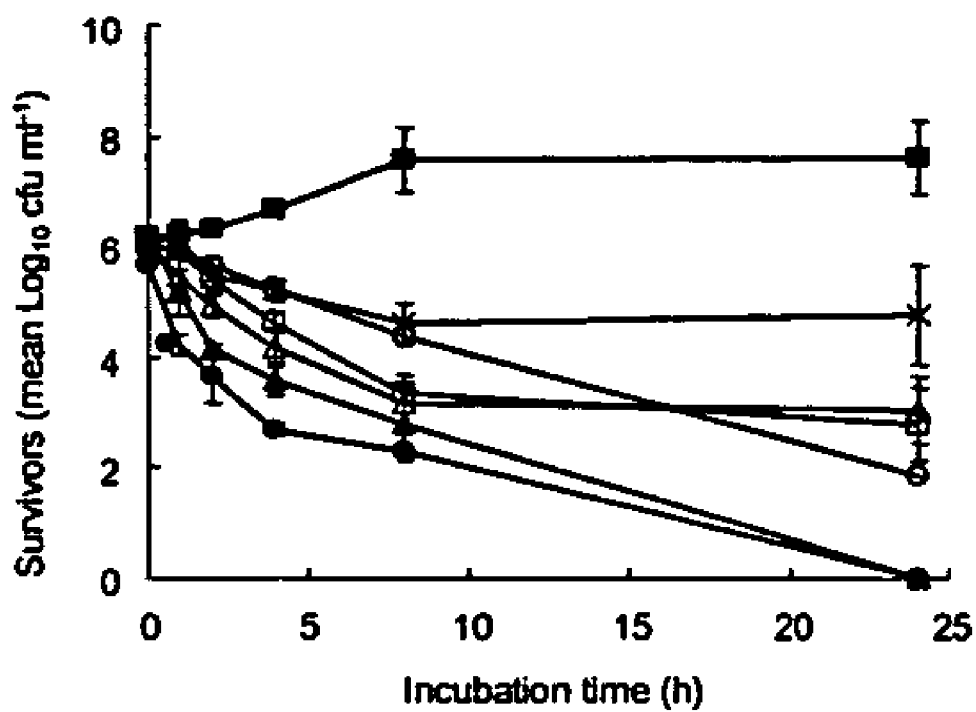
FIG. 10. Time-Killing curves for S. mutans. S. mutans GS-5 was exposed to each agent at MIC (12.5 µM for each peptide and 2 µM for chlorhexidine). Values are the means of two experiments. Control (■), MUC7 12-mer-L (Δ), MUC7 12-mer-D (□), MUC7 20-mer (▲), Hsn5 12-mer (×), magainin II (●), chlorhexidine (○).

The results of the time-kill kinetic studies are summarized in FIG. 10. The killing was time-dependent within 24 h of incubation. MUC7 12-mer-L exhibited similar time-killing pattern to MUC7 12-mer-D. At the MIC (equal potent concentration), Magainin II (25 µM or 61.7 µg/ml) and

TABLE 5

| Test agent | $MBIC_{50}$ (µM) | $MBIC_{50}$ (µg/ml) | $MBEC_{50}$ (µM) | $MBEC_{50}$ (µg/ml) |
|---|---|---|---|---|
| MUC7 12-mer-L | 12.5 | 19.5 | 50 | 78 |
| MUC7 12-mer-D | 6.25 | 9.5 | 25 | 38 |

TABLE 5-continued

| Test agent | MBIC$_{50}$ | | MBEC$_{50}$ | |
|---|---|---|---|---|
| | (μM) | (μg/ml) | (μM) | (μg/ml) |
| MUC7 20-mer | 6.25 | 15.5 | 25 | 62 |
| Hsn5 12-mer | 25 | 39 | >50 | >78 |
| Magainin II | 25 | 62 | >50 | >125 |
| Chlorhexidine | 1.25 | 0.625 | >20 | >10 |

*MBIC$_{50}$: Minimum biofilm inhibition concentration was defined as the lowest drug concentration that showed 50% or more inhibition on the formation of biofilm.
†MBEC$_{50}$: Minimum biofilm eradication concentration was defined as the lowest drug concentration that showed 50% or more eradication of biofilm.

Figure 12:
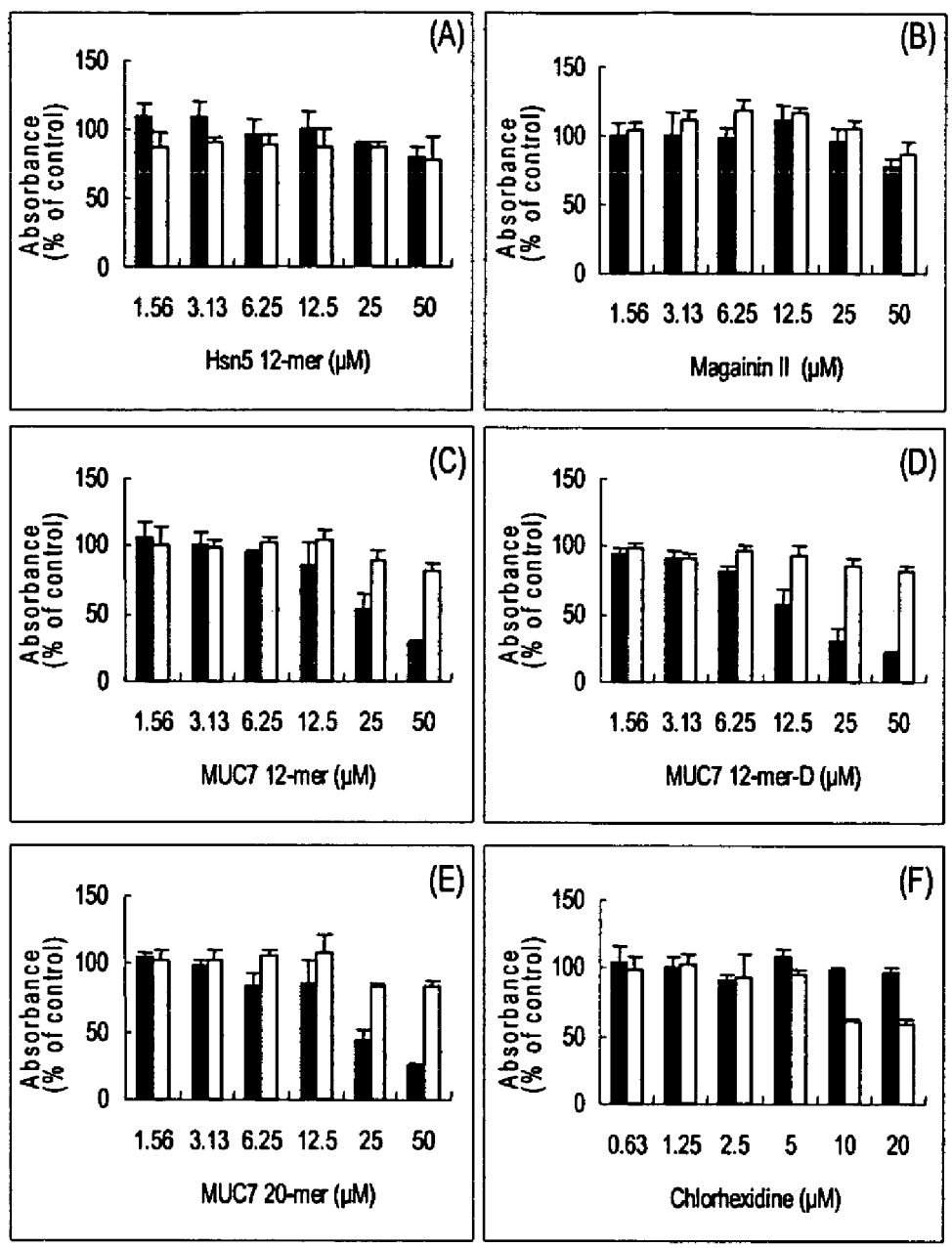
FIG. 12. Effect of peptides on 1-day biofilm of S. mutans. One-day mature biofilm was prepared as described above. BHI medium supplemented with 1% sucrose (BHIS) with peptides, prepared in another microtiter plate, was then transferred to the biofilm plate. After further incubation at 37° C. for 24 h, the biofilm was fixed, stained, and quantified as describe above. Data represents mean and SD of two independent tests performed in duplicated. Empty bar: growth, solid bar: biofilm.

Generally, the inhibition of the *S. mutans* biofilm formation corresponds to the inhibition of bacterial growth. However, for the 1-day developed biofilm (FIG. 12), the reduction of biofilm was observed in the presence of MUC7 12-mer, MUC7 12-mer-D, or MUC7 20-mer at or more than MBEC$_{50}$, while the growth did not decrease in parallel. This indicates that MUC7 peptides exerted eradication activity on the 1-day developed biofilm. The eradication was not observed in the presence of Hsn5 12-mer or Magainin II.

However, in terms of MBIC$_{50}$ or MBEC$_{50}$, we found that MUC7 peptides exhibited not only an inhibitory effect on the formation of *S. mutans* biofilm, but also eradication activity against developed 1-day *S. mutans* biofilm. Therefore, the MUC7 12-mer L and D can be used for the prevention of dental caries by selectively suppressing the growth of *S. mutans*, and exerting the inhibition of the *S. mutans* biofilm formation and eradication of the biofilm.

While this invention has been described through specific examples, routine modifications will be apparent to those skilled in the art and such modifications are intended to be within the scope of the invention.

REFERENCES

1. Bobek, L. A., and H. Situ. 2003. MUC7 20-Mer: Antimicrob Agents Chemother 47:643-52.
2. Satyanarayana, J., H. Situ, S. Narasimhamurthy, N. Bhayani, L. A. Bobek, and M. J. Levine. 2000. J Pept Res 56:275-82.
3. Situ, H., and L. A. Bobek. 2000. Antimicrob Agents Chemother 44:1485-93.
4. Situ, H., G. Wei, C. J. Smith, S. Mashhoon, and L. A. Bobek. 2003. Biochem J 375:175-82.
5. Wei, G. X., and L. A. Bobek. 2004. J Antimicrob Chemother 53:750-8.
6. Devine, D. A., P. D. Marsh, R. S. Percival, M. Rangarajan, and M. A. Curtis. 1999. Microbiology 145 (Pt 4):965-71.
7. Ruissen, A. L., J. Groenink, P. Krijtenberg, E. Walgreen-Weterings, W. van't Hof, E. C. Veerman, and A. V. Nieuw Amerongen. 2003. Biol Chem 384:183-90.
8. Schmidtchen, A., I. M. Frick, E. Andersson, H. Tapper, and L. Bjorck. 2002. LL-37. Mol Microbiol 46:157-68.
9. Chen, H. C., J. H. Brown, J. L. Morell, and C. M. Huang. 1988. FEBS Lett 236:462-6.
10. Avrahami, D., and Y. Shai. 2003. Biochemistry 42:14946-56.
11. Bessalle, R., A. Kapitkovsky, A. Gorea, I. Shalit, and M. Fridkin. 1990. FEBS Lett 274:151-155.
12. Hamamoto, K., Y. Kida, Y. Zhang, T. Shimizu, and K. Kuwano. 2002. Microbiol Immunol 46:741-9.
13. Sajjan, U. S., L. T. Tran, N. Sole, C. Rovaldi, A. Akiyama, P. M. Friden, J. F. Forstner, and D. M. Rothstein. 2001. Antimicrob Agents Chemother 45:3437-44.
14. Takakura, N., Sato, Y., Ishibashi, H., Oshima, H., Uchida, K., Yamaguchi, H. & Abe, S. (2003) *Microbiol. Immunol.* 47, 321-326.

What is claimed is:

1. An isolated and purified peptide of SEQ ID NO:1, wherein all of the amino acids are D amino acids.

2. A method of killing bacteria or fungi comprising the steps of exposing the bacterial or fungal cells to a bactericidal or fungicidal composition comprising the peptide of claim 1.

3. The method of claim 2, wherein the bacteria are selected from the group consisting of, *Escherichia coli, Streptoccocus gordonii, Streptococcus mutans, Actinobacillus actinomycetemcimitans* and *Pseudomonas gingivalis*.

4. The method of claim 2, wherein the bacteria are present in a biofilm.

5. The method of claim 4, wherein the biofilm is present in the oral cavity.

6. The method of claim 5, wherein the bacteria in the biofilm comprise *S. mutans*.

7. The method of claim 2, wherein the fungi are selected from the group consisting of *Candida albicans, Candida glabrata, Crytococus neoformans, Candida krusei* and *Saccharomyces cerevisiae*.

8. The method of claim 2, wherein the peptide is used at a concentration of 25 to 200 μM.

9. The method of claim 8, wherein the peptide is used at a concentration of about 100 μM.

10. The method of claim 9, wherein the peptide is used with EDTA at a concentration of about 1 mM.

11. An oral composition comprising the peptide of claim 1.

12. The oral composition of claim 11 further comprising ethylenediaminetratra acetic acid (EDTA).

13. The oral composition of claim 12, wherein the EDTA is present at a concentration of between 0.5 to 2.0 mM.

14. The oral composition of claim 13, wherein the EDTA is present at a concentration of about 1 mM.

* * * * *

UNITED STATES PATENT AND TRADEMARK OFFICE
CERTIFICATE OF CORRECTION

PATENT NO. : 7,271,239 B2  Page 1 of 1
APPLICATION NO. : 11/213245
DATED : September 18, 2007
INVENTOR(S) : Bobek It is certified that error appears in the above-identified patent and that said Letters Patent is hereby corrected as shown below:

Title Page, Item [*] Notice: Subject to any disclaimer, the term of this patent is extended or adjusted under 35 USC 154(b) by 124 days Delete the phrase "by 124 days" and insert -- by 123 days --

Signed and Sealed this

Twenty Second Day of April, 2008

JON W. DUDAS
*Director of the United States Patent and Trademark Office*